United States Patent [19]
Castano

[11] Patent Number: 6,113,537
[45] Date of Patent: *Sep. 5, 2000

[54] OPTICAL METHOD AND DEVICE FOR DETERMINING BLOOD GLUCOSE LEVELS

[76] Inventor: Jaime A. Castano, 1931 Ralston Ave., Richmond, Calif. 94805

[*] Notice: This patent is subject to a terminal disclaimer.

[21] Appl. No.: 08/950,817

[22] Filed: Oct. 15, 1997

Related U.S. Application Data

[63] Continuation-in-part of application No. 08/634,849, Apr. 19, 1996, Pat. No. 5,713,353.

[51] Int. Cl.$^7$ ........................................... A61B 5/00
[52] U.S. Cl. ..................... 600/300; 600/316; 128/897; 128/898
[58] Field of Search ..................... 600/300, 301, 600/310, 316, 319, 558; 128/897, 898; 351/206, 222, 223, 239, 244; 356/23, 25

[56] References Cited

U.S. PATENT DOCUMENTS

| | | |
|---|---|---|
| 3,761,921 | 9/1973 | Adler et al. . |
| 3,807,839 | 4/1974 | Sugarman et al. . |
| 3,814,510 | 6/1974 | Adler et al. . |
| 3,963,019 | 6/1976 | Quandt . |
| 4,012,128 | 3/1977 | Regan . |
| 4,014,321 | 3/1977 | March . |
| 4,324,460 | 4/1982 | Daley . |
| 4,750,830 | 6/1988 | Lee . |
| 4,789,234 | 12/1988 | Ginsburg et al. . |
| 4,832,480 | 5/1989 | Kornacker et al. . |
| 5,065,767 | 11/1991 | Maddess . |
| 5,086,229 | 2/1992 | Rosenthal et al. . |
| 5,209,231 | 5/1993 | Cote et al. . |
| 5,223,865 | 6/1993 | Shirao et al. . |
| 5,398,681 | 3/1995 | Kupershmidt . |
| 5,433,197 | 7/1995 | Stark . |
| 5,448,992 | 9/1995 | Kupershmidt . |
| 5,485,230 | 1/1996 | Zimmerman . |
| 5,713,353 | 2/1998 | Castano .................. 600/300 |

FOREIGN PATENT DOCUMENTS

WO 95/29627  11/1995  WIPO .

OTHER PUBLICATIONS

Volbrecht et al., "Diabetic Short–Wavelength Sensitivity", Investigative Opth. & Vis. Science, vol. 35, No. 3, Mar. 1994.

Barlow, R.B., Jr., Boudreau, E.A. and Pelli, D.G. 1993. "Metabolic Modulation of Human Visual Sensitivity," *Invest. Ophthamol. Vis. Sci. Suppl.* 43:785.

Kaplan, E. et al., 1988. "Color and Luminace Contrast as Tools for Probing the Primate Retina," *Neurosci. Res. Suppl.* 8:S151.

Macaluso, C., Onoe, S. and Niemeyer, G. 1992. "Changes in Glucose Level Affect Rod Function More than Cone Function in the Isolated, Perfused Cat Eye." *Invest. Ophthalmol. Vis. Sci.* 33(10):2798–808.

McFarland, R.A. and Forbes, W.H. 1940. "The Effects of Variations in the Concentration of Oxygen and Glucose Adaption." *J. Gen. Physiol.* 24:69.

(List continued on next page.)

*Primary Examiner*—Linda C. M. Dvorak
*Assistant Examiner*—Bryan K. Yarnell
*Attorney, Agent, or Firm*—Fish & Richardson P.C.

[57] ABSTRACT

Blood glucose levels of a person are determined by a device which provides a light pattern which varies in regard to one or several parameters defining its luminance, color, rate of flicker, spatial contrast, detail content, speed or otherwise provided that the pattern has first and second appearances and can be shifted from one appearance to the other by changing one or more parameters. A person observes the light pattern and a subjective visual effect which correlates with a corresponding blood glucose level. Thus, the person's glucose level is accurately determined in a completely non-invasive manner.

18 Claims, 13 Drawing Sheets

OTHER PUBLICATIONS

Purpura, K, Kaplan, E., and Shapley, R.M., 1988. "Background Light and the Contrast Gain of Primate P–and M–Retinal Ganglion Cells." *Proc. Natl. Acad. Sci. USA* 85:4534.

Schiller, P.H. and Logothetis, N.K., 1990. "The Color–opponent and Broad–band Channels of the Primate Visual Sustem," *Trends in Neurosci.* 13:392.

Schneck. M.E. 1996. "Influence of Blood Glucose Level on Chromatic VEP in Type I Diabetes." In:*Vision Science and It's Applications* Optical Society of America, Washington, D.C., pp. 38–42.

Schneck, M.E., Volbrcht, V.J., and Adams, J.J. 1991. Immediate and Significant changes in SWS Sensitivity Accompany Variations in Blood Glucose in Diabetic Observers. In: *Technical Digest on Noninvasive Assessment of the Visual System.* eds? Optical Society of America, Washington, D.C., vol. 1, pp. 204–7.

Shapley, R., 1990, "Visual Sensitivity and Parallel Retinocortical Channels," *Ann Rev. Psychol.* 41:635–58.

Volbrect. V.J et al. 1994, "Diabetic Short–Wavelength Sensitivity: Variations with Induced Changes in Blood Glucose Level," *Invest. Ophthalmol. Vis. Sci.* 35(3):1243–6.

Winkler, B.S., 1972. "The Electroretinogram of the Isolated Rat Retina," *Vision Res.* 12:1183.

Winkler, B.S., 1975. "Dependence of Rat and Rabbit Photoreceptor Potentials Upon Metaboism in vitro," *Exp. Eye. Res.* 21:545.

OPTICAL METHOD AND DEVICE FOR DETERMINING BLOOD GLUCOSE LEVELS

This application is a continuation-in-part of U.S. Ser. No. 08/634,849, filed Apr. 19, 1996 now U.S. Pat. No. 5,713,353, incorporated herein by reference in full.

FIELD OF THE INVENTION

This invention relates generally to the field of optics and more specifically to a method and device for analyzing a patient's perception of a light pattern having a plurality of different visual characteristics, and relating such to the patient's blood glucose level.

BACKGROUND OF THE INVENTION

More than ten million people in the United States of America suffer from diabetes, a deficiency in the ability to regulate blood glucose levels. Individuals afflicted with the disease must control their blood glucose levels by measuring their blood glucose levels as frequently as possible and adjusting their food intake, level of physical activity and insulin dosage to regulate the glucose level. Blood glucose level is measured using one of several available invasive techniques.

Invasive techniques require a blood sample from the patient each time an analysis is to be performed. An accurate laboratory blood analysis requires about 5 to 10 ml of blood, and analysis using a laboratory instrument designed for performing such a biochemical analysis. However, the results of the test often are not available for several hours, and sometimes days. In addition, the instruments necessary to perform such an analysis are expensive and require that the blood samples be taken and analyzed by trained technicians.

Another invasive technique, referred to as a "finger stick" uses an integrated, self-contained instrument that evaluates a much smaller blood sample (approximately 0.25 ml). The small blood sample is obtained by puncturing a finger with a small lancet. The sample is then placed on a chemically treated carrier and inserted into the instrument. The finger stick devices normally provide the glucose concentration results in a few moments. However, they are still costly, and require that patient puncture a finger several times per day.

More recently, portable finger stick instruments have become available which require the use of single use, disposable, chemically treated carrier "strips". Although the portable instruments have a relatively low cost (about $100 to $300), the cumulative cost to diabetics for the normal supply of disposable carrier strips is considerable.

Invasive techniques for glucose analysis are problematic and suffer from poor compliance. Although diabetics can forestall the debilitating and often fatal complications of diabetes by frequent monitoring and control, only a small fraction of diabetics monitor their glucose levels as regularly as recommended. Diabetics find the current invasive methods of blood glucose monitoring painful, inconvenient and costly. To encourage frequent monitoring and control there is a clear need for a glucose monitor that requires no blood samples, is easy and convenient to use, is portable, and costs less than current methods.

Non-invasive methods for measuring blood glucose have been described. These methods include measurement of the optical polarization of light in the eye; the absorption, transmission, or scatter of infrared light in body tissue; or the chemical analysis of interstitial fluid removed through the skin by reverse iontophoresis (see, e.g., Rosenthal et al., U.S. Pat. Nos. 5,086,229; 5,279,543; Cote et al., *IEEE Trans. of Biomed. Engineer.* (1992) 39:752–56). However, to date none of these techniques has resulted in a commercially useful instrument. All of these methods have serious technical problems due to the small signals available and the inherent variability of measurements in live tissue. Furthermore, due to the complexity of the implementation, these methods are not likely to lead to small, low-cost instruments that will encourage frequent testing by diabetics.

SUMMARY OF THE INVENTION

We have found that the sensitivity of the visual system to alternating changes in luminance, or luminance contrast, changes with blood glucose concentration in a predictable and precise manner. This property can be used to determine blood glucose non-invasively: one can measure the sensitivity of the visual system to luminance contrast, and from this measurement one can determine the existing blood glucose concentration via calibration data that relates the blood glucose levels that correspond to different values of luminance contrast sensitivity.

One aspect of the invention is a method for determining the concentration of glucose in a subject's blood, by providing a light stimulus having two or more visual characteristics (e.g., a luminance contrast pattern), allowing the subject to observe the stimulus, and correlating the subject's observations with a previously determined calibration curve. In one embodiment of the invention, the subject varies a parameter of the pattern until a subjective change in the pattern appears, and the threshold or crossover point is compared with a calibration curve.

Another aspect of the invention is a device for determining the concentration of glucose in a subject's blood, by providing a variable-parameter light stimulus (e.g., a luminance contrast pattern), which comprises a body member, a display means for generating a light stimulus, and optionally actuator means for initiating the display and/or for indicating when a crossover or change is observed.

An object of the invention is to provide a non-invasive optical means of determining a patient's blood glucose level. Another object is to provide the non-invasive means for determining glucose levels by using images or light patterns which provide visual stimulation to the retina and determining with such images or light patterns changes that take place in a patient's retina in response to changes in blood glucose levels.

These and other objects, advantages and features of the present invention will become apparent to those persons skilled in the art upon reading the details of the structure, methodology and usage as more fully set forth below with reference being made to the accompanying figures forming a part hereof.

DETAILED DESCRIPTION OF THE INVENTION

Figure 1:
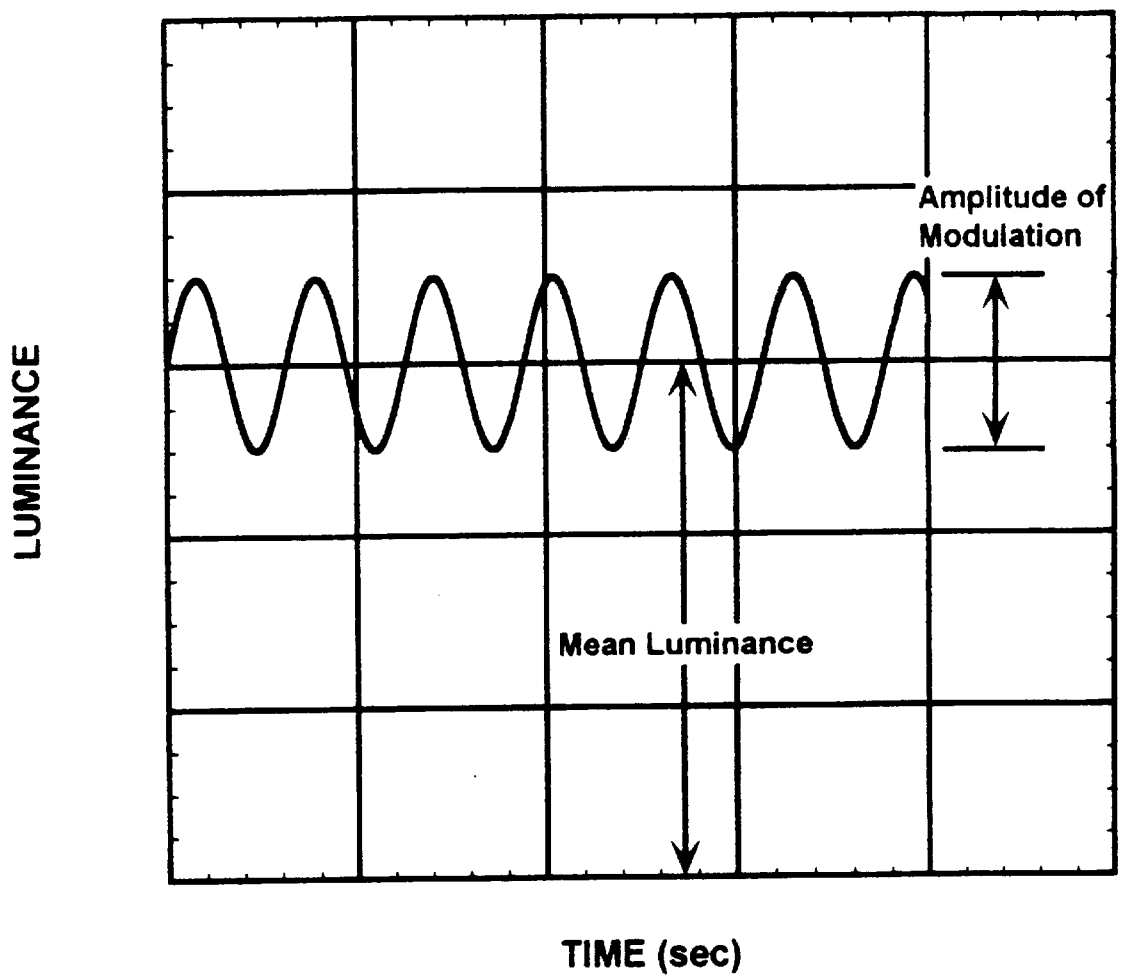
FIG. 1 is a graph which shows the relationship between luminance, mean luminance, and amplitude of modulation for a flickering light source.

Before the present optical method and device for determining blood glucose levels is described, it is to be understood that this invention is not limited to the particular process steps, light changing, light stimulus or other steps and components described as such may, of course, vary. It is also to be understood that the terminology used herein is for the purpose of describing particular embodiments only, and is not intended to be limiting since the scope of the present invention will be limited only by the appended claims.

The singular forms "a", "an" and "the" include plural reference unless the context clearly dictates otherwise. Thus, for example, reference to "a changing light stimulus" refers to one or more changing light stimuli, reference to "an actuation means" refers to one or more means and so forth.

Unless defined otherwise all technical and scientific terms used herein have the same meaning as commonly understood by one of ordinary skill in art to which this invention belongs. Although methods and materials similar or equivalent to those described herein can be used in the practice or testing of the present invention, the preferred methods and materials are now described. All publications mentioned hereunder are incorporated herein by reference.

The publications discussed herein are provided solely for their disclosure prior to the filing date of the present application. Nothing herein is to be construed as an admission that the invention claimed herein is not entitled to antedate such publications by virtue of prior invention.

It is well understood that glucose is present in blood and can migrate to all tissues via the circulatory system. In particular glucose is an important metabolite for the retina. The retina possesses a high rate of metabolic and electrical activity which is almost exclusively fueled via the oxidative breakdown of glucose (W. K. Noell, *Am. J. Physiol.* (1959) 48:347; B. S. Winkler, *Exp. Eye Res.* (1975) 21:545). The retina obtains the required glucose from an abundant blood supply provided to the retina via the retinal choroid capillaries. Not only does the retina utilize glucose for its metabolic and electrical activity, but the retina is able to consume glucose in proportion to the amount of glucose available over a wide range of glucose levels (A. Ames III et al., *J. Neurophysiol.* (1963) 26:617; B. S. Winkler, *Vision Res.* (1972) 12:1183; B. S. Winkler, *J. Gen. Physiol.* (1981) 77:667).

In view of the above it can be anticipated that changes in the blood glucose concentration will have noticeable effects on the visual system. Such effects have been demonstrated by others in areas unrelated to the subject of this invention. Specifically, glucose concentration affects rod-mediated responses in the perfused cat eye (C. Macaluso, et al., *Invest. Ophthalmol. & Visual Science, Supp.* (1991) 32:903); high blood glucose concentration decreases the detection thresholds with respect to low-contrast patterns and increases the ERG amplitude in humans (R. B. Barlow, Jr., et al., *Invest. Ophthalmol. & Visual Science, Supp.* (1993) 34:785); and lastly, low blood glucose concentrations increase dark-adapted detection thresholds in humans (R. A. McFarland et al., *J. Gen. Physiol.* (1940) 24:69).

This demonstrates that the ability of an individual to perceive certain types of visual stimuli changes with fluctuations in blood glucose level. Based on this it can be understood that the appearance of some images can change with changes in blood glucose level. The present invention utilizes this basic principle to provide a method and device which calculates blood glucose levels based on changes in the appearance of a specially designed visual stimulus.

The present invention relies on the fact that subjectively observable phenomena vary depending on the concentration of glucose in the blood. It is currently believed that some visual subsystems are controlled by distinct groups of cells, and that some subsystems have different degrees of sensitivity to glucose concentration. However, the invention can be practiced without an understanding of the underlying causes: whatever the cause, subjective visual phenomena exist that vary with glucose concentration. In general, luminance contrast can be used to stimulate different visual subsystems to varying degrees, thus creating subjective visual effects.

The sensitivity of the visual system to luminance contrast can be measured using a number of methods. The following are three examples of suitable methods.

Method a) Threshold for Flicker

Figure 2:
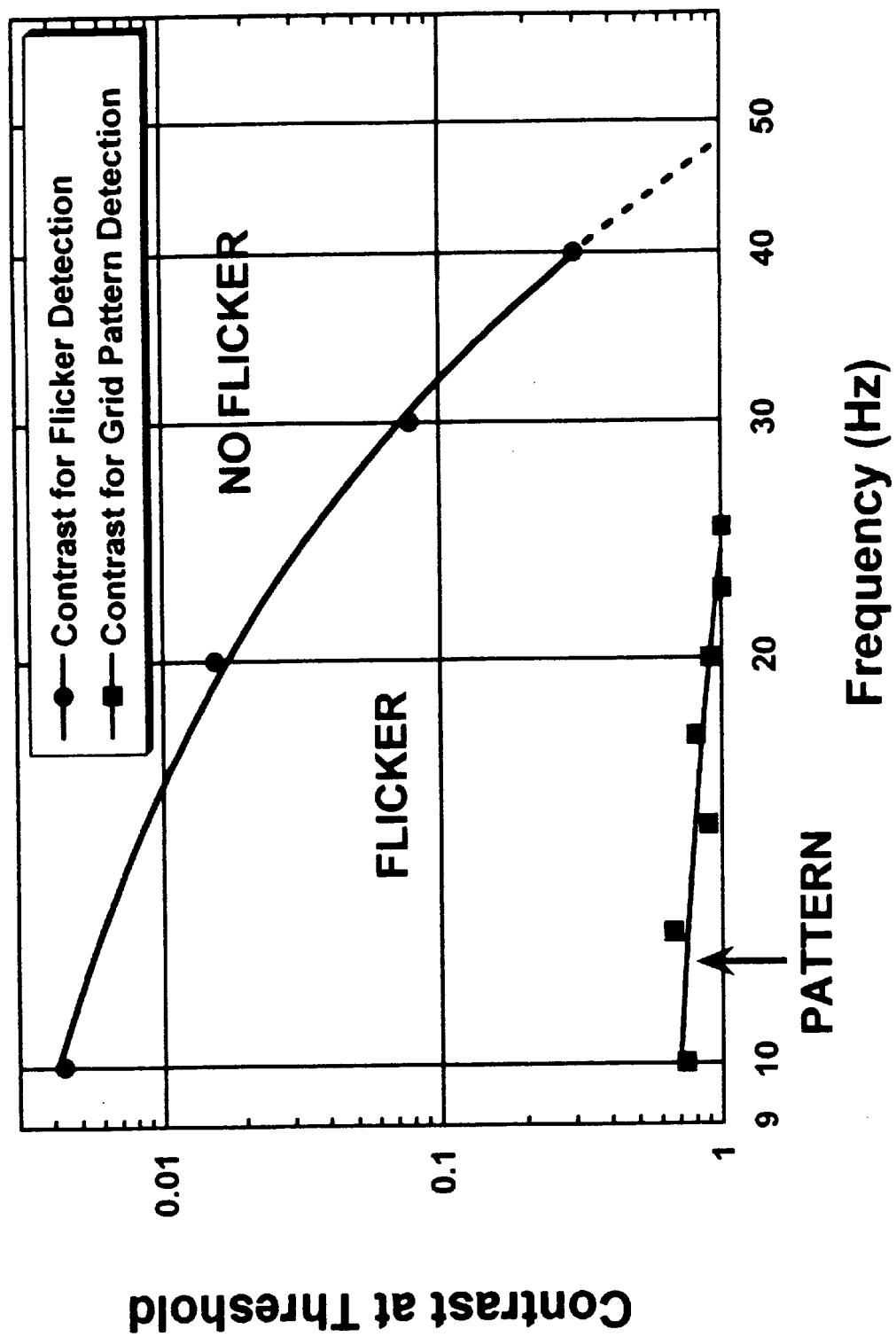
FIG. 2 is a graph showing the crossover point for a flickering source as a function of contrast and flicker frequency.

One can use a light pattern whose luminance changes over time, and can determine the minimum change in luminance that causes the subject to notice the luminance change. The ability of a subject to detect "flicker" in a fluctuating light source or image depends on the rate of fluctuation and the contrast (or depth of modulation): above a certain rate of change (typically around 48 Hz), one cannot detect flicker visually, a principle exploited by movies, television and computer monitors. A subject's sensitivity to flicker at a set frequency depends on the amount by which the luminance varies: above or below the optimal frequency, the contrast must be increased in order to detect flicker. One can plot a curve of the subject's detection of flicker as a function of contrast and frequency, as shown in FIG. 2. The position of the curve shifts, depending on the subject's glucose concentration.

The luminance changes can consist of regular alternations in luminance, such as shown in FIG. 1. The mean luminance of this pattern may be constant and the amplitude of modulation may be adjustable. The ratio of one-half the amplitude of modulation to the mean luminance is the temporal luminance contrast, or luminance contrast for short. One can use this pattern to measure the sensitivity of the visual system to luminance contrast by determining the minimum luminance contrast that makes the changes in luminance noticeable to the subject (contrast at threshold).

When one measures the threshold contrast at different frequencies of modulation one obtains a graph such as that shown in the upper plot of FIG. 2. These data were obtained for one subject at 4 frequencies, and show at each frequency the minimum contrast needed for the subject to see the luminance alternations, that is, to see flicker in the light pattern. In this plot, the vertical axis indicates the ratio of the amplitude of modulation to the mean luminance, or temporal luminance contrast of the light pattern at the point when the alternations in luminance become just visible. Thus the vertical axis is a convenient scale to measure the sensitivity of the visual system to the luminance alternations: the higher one goes on the vertical axis, the smaller the modulation needed to make the alternations just visible and thus the greater the sensitivity of the visual system to luminance alternations. The bottom end of the scale, shown as contrast value of 1, indicates the maximum modulation possible in the light pattern: the luminance of the pattern is alternating between a maximum of twice the mean luminance and a minimum of zero luminance. A data point at this level would indicate conditions of minimum sensitivity of the visual system to luminance alternations, since it would mean that under such conditions, it would take the maximum modulation possible to make the alternations visible. The horizontal axis is the frequency of the luminance alternations.

Thus, the upper plot of FIG. 2 represents the sensitivity of the visual system to luminance alternations of various frequencies. Of the 4 frequencies tested, sensitivity is maximum at 10 Hz and minimum at 40 Hz. The area of the graph above this plot indicates frequency-contrast combinations that produce the sensation of steady illumination, i.e. absence of flicker. Below this plot is a region where flicker is seen. Near 48 Hz the plot intersects the horizontal axis, indicating the maximum frequency at which flicker can be seen under the conditions tested. The plot indicates that, under the test conditions used, the sensitivity of the visual system to luminance alternations decreases steadily for frequencies above 10 Hz, and that approximately 48 Hz is the maximum frequency at which flicker can be seen.

Different testing conditions yield a similar sensitivity plot but with slightly different shape. In particular, the height and the width of the plot change with the size of the pattern, the location of the retina where the pattern is imaged, and the mean luminance of the pattern. The data shown above was measured with a circular field 5 degrees in diameter, red in color, imaged in the central fovea, and with mean luminance of 30 $cd/m^2$.

Figure 3:
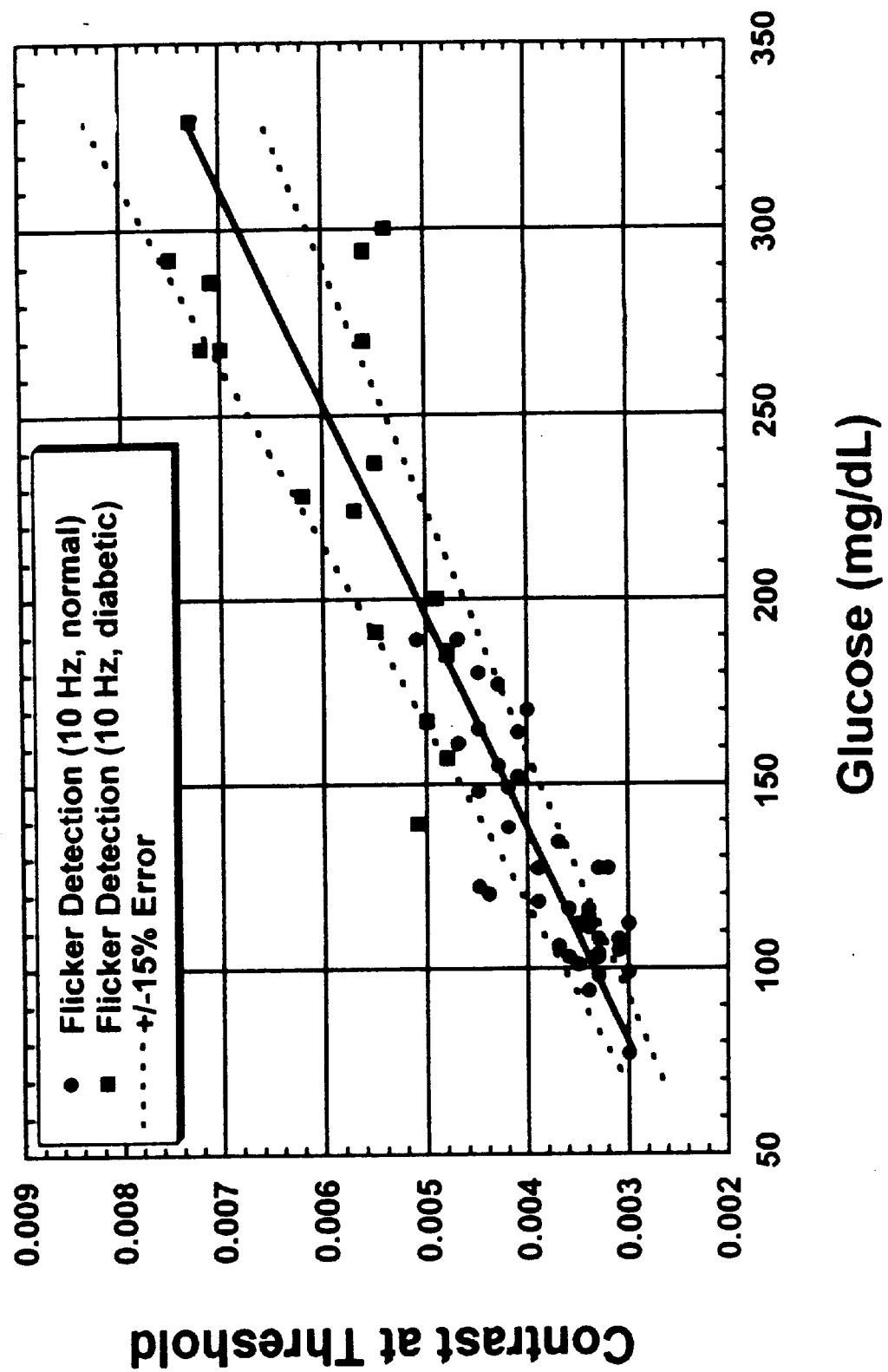
FIG. 3 is a graph which shows how the crossover point changes as blood glucose level changes.

If the sensitivity of the visual system to luminance contrast decreases, the resulting plot would be lower in the vertical scale, indicating that larger luminance contrasts are needed to detect flicker. FIG. 3 shows that at higher blood glucose levels, the luminance contrast sensitivity of a subject decreases at all frequencies between 10 and 40 Hz. To measure the sensitivity of the visual system to luminance alternations, one does not have to plot the entire luminance contrast sensitivity graph described above. It is sufficient to determine one point on the graph, that is, one combination of contrast-frequency that causes the flicker to just become visible. One can determine one point in the graph in a variety of ways. For example, one can keep the frequency constant and vary the luminance contrast of the light pattern until one finds the flicker-no flicker threshold. This is equivalent to seeking the flicker/no flicker boundary by moving in the sensitivity plot along a vertical line centered on the fixed frequency. Alternatively, one can fix the luminance contrast and vary the frequency, looking for the frequency that causes the flicker/no flicker transition. This is equivalent to moving in the sensitivity plot along a horizontal line corresponding to the fixed contrast until one finds the flicker-no flicker transition. A combination of the above two methods, that is, seeking the flicker/no flicker boundary by adjusting both contrast and frequency could also be used. Example 1 below shows a case in which the flicker threshold is measured by keeping the frequency constant while varying the luminance contrast. The thresholds so measured followed blood glucose levels.

Method b) Threshold for a Subjective Visual Effect

A second method of measuring the luminance contrast sensitivity is to determine the minimum luminance contrast that elicits a certain visual effect. For example, at higher luminance contrast levels than those needed to just see flicker, observers report subjective visual effects such as the appearance of geometric patterns, colors (i.e., colors other than a color that is actually displayed to the observer), radial movement, square or hexagonal grid patterns, etc.

The lower plot in FIG. 2 is an example of data taken on the same subject as the upper plot and shows, at each of a number of frequencies, the minimum contrast which elicited the subjective visual effect of a regular grid pattern. Thus, at a frequency of 10 Hz it was necessary to increase the contrast of the light pattern to 0.7 to elicit the sensation of a grid pattern, and near 20 Hz it was necessary to increase the contrast to 1.0, or its maximum level. At higher frequencies it was not possible to elicit the grid pattern effect. The resulting plot is another representation of the sensitivity of the visual system to luminance alternations of different frequencies. The area beneath the plot indicates contrast-frequency combinations that elicit the visual effect of a grid pattern. The occurrence of the visual effects associated with the fluctuations in luminance in the light pattern can be used to measure the sensitivity of the visual system to luminance alternations. As was the case with the flicker sensitivity, if the sensitivity of the visual system to luminance contrast were to decrease, as is the case when blood glucose rises, the lower plot in FIG. 2 would shift downward, indicating larger luminance contrast needed for the subject to perceive the visual effect. Also, as was the case with the flicker sensitivity, one can measure the visual effect threshold at one point in the graph, by approaching the visual effect/no visual effect boundary from a number of directions in the contrast-frequency space. Thus one can fix the frequency and vary the contrast, fix the contrast and vary the frequency, or use a combination of these methods. Example 2 shows a case in which the thresholds for the subjective visual effect of radial movement or appearance of a grid pattern were sought by keeping the luminance contrast constant at the maximum level of 1, while varying the frequency. The threshold values of frequency so measured followed blood glucose levels.

Method c) Comparison of Two Subsystems

The visual system contains parallel sub-systems or channels that process different aspects of a visual stimulus. It is possible to measure the sensitivity of one channel, for example the channel that processes the luminance contrast, by comparing its sensitivity relative to another channel. For example, one can stimulate the visual system with a light pattern that contains two parameters: temporal luminance contrast and color contrast. The pattern can be such that it causes a subjective visual effect that changes with the relative strength of the two parameters. Thus one can alter the value of one or both of the parameters until a desired subjective visual effect is noticed. The relative value of luminance contrast and color contrast when the visual effect occurred is a measure of the sensitivity of the luminance contrast channel relative to the color contrast channel.

The sensitivity of the luminance channel relative to other channels, such as the color contrast channel, changes when blood glucose level shifts. Thus the relative values of the luminance contrast and color contrast when the desired visual effect is noticed follows changes in blood glucose levels and can be used to determine blood glucose levels.

Example 3 below shows a case where luminance contrast and color contrast are made to cause motion in opposite directions in a windmill pattern, and the relative values of luminance contrast and color contrast at the point of no motion follows blood glucose levels.

Any of the luminance contrast sensitivity measurements described above can be made using one of several specific techniques known in vision psychophysics. For example, one technique involves presenting a predetermined number of contrast levels, several times each, and finding the fraction of times that the subject sees each stimulus level. The threshold is chosen as the contrast value that caused the stimulus to be seen, for example, 50% of the times.

A second technique is the staircase, which uses an interactive approach: the stimulus level on each trial is chosen on the basis of the observer's response to the previous trial. In this way, the observer "walks" the visual parameter to the level where the desired effect is found.

A third technique uses a continuous stimulus display rather than single-value presentations. With this technique, the observer uses a knob or keypad to change some aspect of the display (e.g. the contrast level). When the observer is satisfied that the stimulus parameter is at the appropriate level (e.g. the flicker is just visible), the device records the stimulus parameters at that instant.

The above three techniques are examples of sequential presentations. Alternatively, spatial presentations can be used advantageously in that the overall measurement time can be shortened relative to sequential presentations. In the spatial presentation technique, visual stimuli of different strengths are presented simultaneously side by side, for example lights or sections of a continuous light display modulated at different luminance contrast, or driven at different frequencies. The subject examines the array and chooses the location of the stimulus that has the desired characteristic, for example the light or segment of the display that just flickers, or the light or segment of the display that shows the desired characteristic.

Another useful technique involves a combination of the sequential and spatial techniques. An observer may determine which of a set of spatially distinct lights elicited an effect on the first trial. Then the lights or segments of the display are re-assigned parameter values and the trial repeated several times. This combination technique yields a more accurate and efficient measurement of the observer's sensitivity.

Other techniques for measuring sensitivity of visual mechanisms accurately involve presenting several alternatives to the subject and forcing the subject to respond which of the alternatives presented contained the desired visual characteristic. This technique avoids the subject's bias and yields very accurate sensitivity measurements.

Definitions

The term "light pattern" as used herein refers to an image which can produce two or more subjective visual impressions, or subjective characteristics, on an observer, where the subjective characteristic can be shifted from one to another by altering a controllable parameter. For example, a light pattern within the scope of this invention may be a light source that varies in luminance at a regular rate. Under certain frequencies of variation, and degrees of contrast between the "high" and "low" levels of luminance, an observer perceives a flicker in the image. By changing one or more parameters of the light pattern, for example by decreasing the luminance contrast and/or by increasing the rate of alternation (frequency), the subjective visual impression (flickering source) can be changed to a second visual impression (steady source): the flickering effect disappears. Note that either impression may constitute the "first subjective characteristic", i.e., either "flicker" or "no flicker" may be the first characteristic, and either may be the second characteristic. Examples of light patterns include, without limitation, a flickering source (a source which alternates between a high luminance level and a lower luminance level), a radial vane pattern (e.g., a windmill pattern, which produces the illusion of rotation), a checkerboard of alternating luminance levels and/or colors, and the like.

The term "crossover point" as used herein refers to the point at which a first subjective characteristic changes to a second subjective characteristic, for example, the point at which a flicker source appears to stop flickering (or at which a steady source appears to begin flickering), or the point at which a rotating image appears to stop and change direction.

The term "parameter" as used herein refers to any aspect of the light pattern that may be altered to produce a change in visual subjective characteristic. Examples of parameters within the scope of the invention include, without limitation, color, luminance level, contrast, shape, size, position, detail content, texture, speed of movement or rotation, direction of movement or rotation, rate of change, and the like. The parameter may vary in time or in space. For example, the luminance of the light pattern may be varied with time over all or part of the pattern, or the luminance may be smoothly varied from one part of the pattern to another. Alternatively, the pattern may be provided as a plurality of regions, with each region have a different value of the parameter. For example, a flickering source pattern may be provided having the same alternation rate throughout, but having a different degree of contrast in each of a plurality of regions. As another example, the light pattern may be a plurality of rotating vane images, having a different contrast between the vanes in each image, where the observer simply selects the image that does not appear to be rotating.

The term "correlating" as used herein means to associate the parameter associated with a selected visual characteristic with the glucose level of the observer's blood. Typically in the practice of the invention, a device is calibrated by having the subject observe a light pattern at a range of different blood glucose concentrations. It is presently preferred to record the crossover point observed for each measured blood glucose concentration, and to use this as the standard curve.

The term "appearance of colors" is used to describe a subjective visual effect occurring at a specific frequency when the retina is stimulated with a flickered light of variable frequency. For example, the appearance of colors can consist of pink and green irregular patches that appear to radiate from the point of fixation.

The term "cessation of radial movement" is used to describe a subjective visual effect occurring at a specific frequency when the retina is stimulated with a flickered light of variable frequency. For example, at lower frequencies, faint shadows like concentric ripples in water radiate from the point of fixation towards the periphery, while at higher frequencies, the shadows travel in the opposite direction. At an intermediate frequency, the radial movement of the shadows ceases momentarily before changing direction; this is the frequency of cessation of radial movement and is an example of a subjective visual effect occurring during the observation of a changing light pattern.

The term "critical parameter value" is used to describe the value of a variable parameter in a changing light pattern, at the point when the subject notices the subjective visual effect.

The term "grid pattern" is used to describe a subjective visual effect occurring at a specific frequency when the retina is stimulated with a flickered light of variable frequency. The effect consists of a regular pattern, which some observers describe as a fine square grid, and others as a fine honeycomb pattern.

The term "luminance" shall mean the quantitative measure of brightness of a light source or an illuminated surface, formally defined as luminous flux per unit solid angle emitted per unit projected area of surface.

Method and Device in General

The device of the invention is preferably a portable, light weight (less than 0.5 kg) device comprised of a body member having positioned thereon a means for generating a light pattern. It is preferably small enough to be hand-held, although it may be adapted for use on a desk or table top. The light pattern stimulates the retina by virtue of the subject looking at the light pattern.

The light pattern either changes over time or provides an array of images having different parameters. In the case of a changing pattern, either the entire light pattern or a part of the light pattern changes over time with respect to one or more different parameters. For example, the parameters may be selected from the group consisting of color, luminance level, contrast, shape, size, detail content, texture, speed of movement, appearance of pattern, direction of movement and rate of flicker. In particular situations it is desirable to use different combinations of variable parameters in order to make the perceived threshhold effect more dramatic. For example, referring to FIG. 4, it may be desirable to vary both the frequency and the contrast simultaneously, to approach the curve at an angle perpendicular to the curve (which therefore maximizes the measurement of any difference).

The light pattern must stimulate the retina in a specific manner. Specifically, the light pattern should be designed to stimulate a retinal system wherein the sensitivity of the system changes with glucose levels. For example, one may provide a light pattern which stimulates the M- and P-systems of the retina, and stimulates these systems in a changing ratio. Preferably in such a case, the M- and P-systems of the retina are continuously and gradually stimulated in an increasing ratio, e.g., the M-system is continuously and gradually stimulated more relative to the P-system.

The stimulation of the retinal systems by the light pattern continues until the patient perceives a subjective visual effect in which the light pattern appears to undergo a change in appearance or to suddenly acquire a quality that was not present before ("crossover effect"). The subjective visual effect may be virtually any perceivable change in the light pattern, and generally consists of a change such as the appearance of color patches, the appearance of a grid pattern or flickering, or the perception of radial movement stopping, starting, or reversing direction. It should be noted that some of such visual effects are perceived effects in that the color patches or the grid pattern are not present in the stimulus at all: the stimulus is a uniform, featureless field of a constant color. Another subjective visual effect which might be noted is the reversal in the direction of rotation of a light pattern. This pattern may not be rotating at all, but rather presenting a series of images that creates the impression or appearance of rotation. That apparent rotation may then reverse direction and the light pattern may then appear to rotate in the opposite direction when the stimulation passes over the crossover point.

Determining +/−Glucose Levels

It should be noted that the present invention can also be implemented as a single-point device—a device which does not provide a blood glucose value, but simply indicates if the blood glucose level is above or below certain value. This information is valuable for some individuals who, for example, wish to maintain their blood glucose concentration above or below a certain level, for example below 200 mg/dL, and who do not need to know what the exact level is. The single-point device is a simpler device in that it does not require patient's input, does not need to perform any calculations or checks and does not need to store look-up tables. The device can be calibrated so that the light pattern has one appearance when the blood glucose level is above 200 mg/dL and a different appearance when the blood glucose level drops below this discrimination point. For example, the light pattern can consist of an apparently-rotating windmill or wheel pattern. The parameters of the pattern—color and luminance of the vanes, frame rate, background luminance, etc.—can be chosen so that for a specific individual the pattern appears to rotate in one direction when the individual's blood glucose level is above 200 mg/dL and in the opposite direction when the individual's blood glucose level drops below that value. Alternatively, the device may display a row or array of windmill images, each having a different fixed value for one or more parameters, such that one can roughly determine the blood glucose concentration by observing which (or how many) images appear to be rotating clockwise or counterclockwise (or by which image appears stationary). Each image may be labeled with the corresponding glucose concentration. For example, the device may display a row of five images, labeled "<100 mg/dL", "130 mg/dL", "160 mg/dL", "190 mg/dL", and ">200 mg/dL." If any image appeared stationary, the subject would take the labeled concentration as the reading. If no image appeared stationary, the subject would know that the actual concentration was in between the images rotating in different directions (e.g., if images 1–3 appear to rotate clockwise, and images 4–5 appear to rotate counterclockwise, the subject would take "160–190 mg/dL" as the current blood glucose concentration).

Another single point device of the invention employs the flickering light technique. In its simplest form, the device presents a single light source, which has been calibrated as to depth of modulation and alternation frequency to provide a flickering appearance below a preset blood glucose concentration, and a steady source appearance above that concentration. Thus, the subject need only activate the device, and determine whether the source appears to flicker or not in order to determine whether the blood glucose concentration is higher than the desired level. This device may also be provided with a row or array of sources, having a different fixed value for one or more parameters. The subject observes the device, and notes the highest source that appears to flicker, and the lowest source that does not appear to flicker, and takes as the glucose concentration the reading ranging from one to the other. In such a multiple flickering source device, the individual sources may be visually separated (e.g., separately enclosed, or provided with separating partitions) to prevent reflection from an adjacent flickering source from causing a "non-flickering" source to appear to flicker.

Calibration

In order to calibrate a device of the invention, it is necessary to establish the relationship between parameter values at the point where the subjective visual effect is noted ("crossover point") and the values of blood glucose concentration that correspond to those points ("corresponding glucose values" or "corresponding blood glucose values"). An example of such a relationship is shown schematically in the graph within FIG. 11, wherein the vertical axis of the graph corresponds to critical parameter values and the horizontal axis represents corresponding glucose values. A simple linear relationship has been assumed in this diagram for illustration purposes.

The relationship between critical parameter values and corresponding glucose values is established by measuring simultaneously or in close time proximity pairs of values, one critical parameter value and its corresponding glucose value. Specifically, the patient views the light pattern in which the variable parameter is changing over time. This change is maintained until the patient notes the subjective visual effect associated with the crossover point. At this point the value of the variable parameter, or critical parameter value is noted, preferably by way of the patient actuating an actuation means such as a key or a button in the device, which actuation prompts the device to record internally the value of the variable parameter at that moment. Simultaneously or substantially contemporaneously with the variable parameter measurement, the blood glucose level of the patient is determined by any conventional means and entered into the memory of the device. Thus, the measurement yields two numbers, the critical parameter value and the corresponding blood glucose level, which are stored into the memory of the device. Alternatively, the subject is presented with a row or array of images having a variety of parameter values, and selects the image or images which meet the desired appearance (e.g., flickering, non-flickering, rotation in a particular direction, and the like), and the parameter values for that image are noted and stored. This process of calibration is repeated several times when the patient's glucose level would be expected to be different. Preferably, readings are taken at very low and very high levels, as well as a number of evenly spaced levels therebetween. Thus, pairs of numbers are stored in the memory of the device, each pair consisting of a critical parameter value and a corresponding blood glucose value. The number of pairs of values needed for a full calibration of the device depends on the shape of the graph that relates parameter values and glucose values, the constancy of this graph from one patient to another, and the accuracy desired in the measurements. The greater the regularity of the graph and the greater the constancy of the graph among patients, the fewer the number of calibration points required for a given degree of desired measurement accuracy. The shape of the graph and its degree of constancy among patients can be determined in clinical tests.

After completing these calibration steps the patient can, thereafter, determine his or her glucose level by viewing the light pattern and noting the point when the subjective visual effect is detected. When the subjective visual effect is noted, the patient actuates a means for noting such, and the actuation prompts the device to record the parameter value at that moment or position. The glucose value that corresponds to the recorded parameter value is then looked up in the table of stored pairs of values, if an exhaustive list has been stored. If an exhaustive list of all possible parameter values has not been stored in memory, the glucose value that corresponds to the recorded parameter value may be calculated by interpolation. For example, the device may look up from memory the stored parameter values that are closest to the recorded parameter value, one greater and one smaller than the recorded parameter value, and assuming a certain relationship, for example a linear relationship, calculate a glucose value in the range between such two stored parameter values.

In an alternative embodiment of the invention, the light pattern is presented in several distinct regions simultaneously, with each region displaying the light pattern with a different value of the variable parameter. The subject then selects the pattern closest to the preselected appearance. For example, the device may display a series of rotating vane ("windmill") patterns, each having a different amount of luminance contrast or color contrast. The subject is then asked to pick the windmill that is stationary (or, alternatively, to pick all windmills that are rotating clockwise, or all that are rotating counterclockwise), and the parameter for the selected image is determined, and the corresponding glucose concentration determined. The procedure is preferably presented several times, with the location of each image randomized, to insure accuracy of measurement, and to insure that the subject does not simply pick the image in one particular position each time. Alternatively, the device may provide an array of flickering sources, each having a different value for one or more parameters. The subject is then asked to select all flickering sources, or all non-flickering sources, or preferably is asked to select first all of one appearance, then all of the other appearance.

Preferably, several determinations of critical parameter values are performed consecutively and automatically by the device, sometimes while the parameter values increase, and sometimes while the parameter values decrease. Several determinations are performed in order to increase the accuracy of the measurement, to remove the effect of reaction time, and to check the consistency of the patient's input. In order to insure accuracy the calibration of the device can be repeated periodically e.g., weekly, monthly, quarterly, or yearly as needed.

If desired, the device may select different values of the parameter for each successive presentation, and may pick values of the parameter that bracket the crossover point more and more closely. For example, the device may first display images having parameter values of 10%, 25%, 50%, 75%, and 90%. If, after one or more presentations, it appears that the crossover point occurs between 50% and 75%, the device may next present images having parameter values of 40%, 50%, 55%, 60%, and 75%. If the crossover point now appears to be between 50% and 55%, the device might next present images having parameter values of 50%, 51%, 52%, 53%, and 54%.

Hand-held Device

Figure 12:
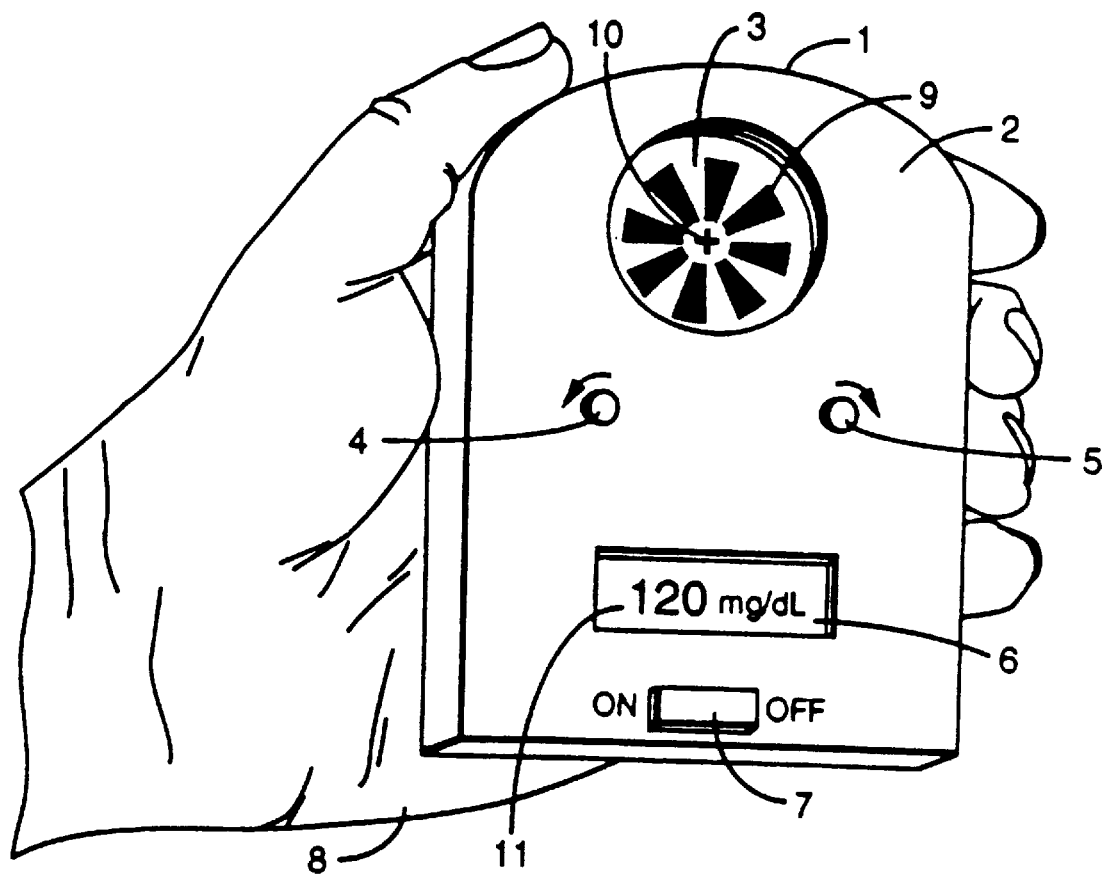
FIG. 12 shows an embodiment of the device.

A hand-held embodiment of a device 1 shown in the FIG. 12 includes a body member 2, a light pattern display 3, patient input switches 4 and 5, alphanumeric display 6 and On/Off switch 7. Other controls or input means (for example, a serial port for interfacing with a computer, not shown) can provide a means for additional input from the patient, such as information regarding meals, exercise or the amount of insulin taken by the patient, or blood glucose levels measured by other means during calibration. Additionally, the device may be provided with a stand or cradle (not shown) so that it may be positioned stably on a desk or tabletop.

The body member 1 is preferably small enough to fit in the patient's hand 8, pocket or purse. The On/Off switch 7 turns the instrument 1 on and off. The light pattern display 3 shows the light pattern, for example an apparently rotating windmill wheel 9. This light pattern could be generated, for example by a combination of LEDs, diffusers, filters and lenses, by a solid state screen, by a CRT, or by any other suitable means via signals sent to the screen from a programmable microprocessor. The light pattern includes a fixation pattern 10 in its center, which the patient gazes at during a measurement, and which is used to direct the line of sight and thus control and maintain the position of the light pattern on the retina. Alternatively, the pattern may be a flickering light, even a single light-emitting diode (LED). The patient input switches 4 and 5 allow entering information about the direction of apparent rotation perceived by the patient. The alphanumeric display 6 provides information to the patient e.g., instructions and prompts during the measurement process, information regarding the quality of the measurement, the calculated blood glucose concentration, and previous measurements recalled from the memory. The characters 11 in the alphanumeric display 6 should be preferably of large enough size to be readable even by patients with reduced visual acuity.

To use the device 1, the patient turns on the instrument, looks at the fixation cross 10 in the center of the light pattern 9 and determines the initial direction of apparent rotation of the wheel. The patient then presses the input button 4 or 5 that corresponds to the direction perceived and continues to observe the pattern. When a reversal in the direction of apparent rotation is perceived, the patient presses the button 4 or 5 corresponding to the new direction of rotation and continues observing the pattern. The patient continues this process of pressing a button 4 or 5 each time the apparent rotation reverses direction, until the instrument determines (via the programmable microprocessor) that enough consistent data has been entered to compute blood glucose concentration with sufficient accuracy. The instrument uses the values of the light stimulus parameters at the times when reversals were observed to compute corresponding glucose levels, using previously entered conversion data entered during calibration as described above. The instrument then stops displaying the light pattern 9 and displays the computed blood glucose concentration in the alphanumeric display 6. If the instrument determines that it cannot compute a reliable answer, it will display one of the messages "High", "Low", or "Unable to Measure".

In another embodiment of the invention, the display contains a field of flickering source images, or a plurality of apparently rotating windmill images. In this case, the actuating means must indicate which image is selected (rather than the time at which a parameter value causes an apparent crossover). Suitable means include, without limitation, a touch-sensitive screen, a cursor (for example, an indicator image that points to each test image sequentially, and permits the subject to indicate the selected image, for example by double-clicking a button), a plurality of buttons (e.g., one button dedicated for each image, or buttons which define X-Y coordinates, such as row 1–3, column A-C). The device may display the images in a randomized fashion, so that the parameter value does not vary smoothly from one image to the next adjacent image, in order to obtain more accurate results.

Figure 13:
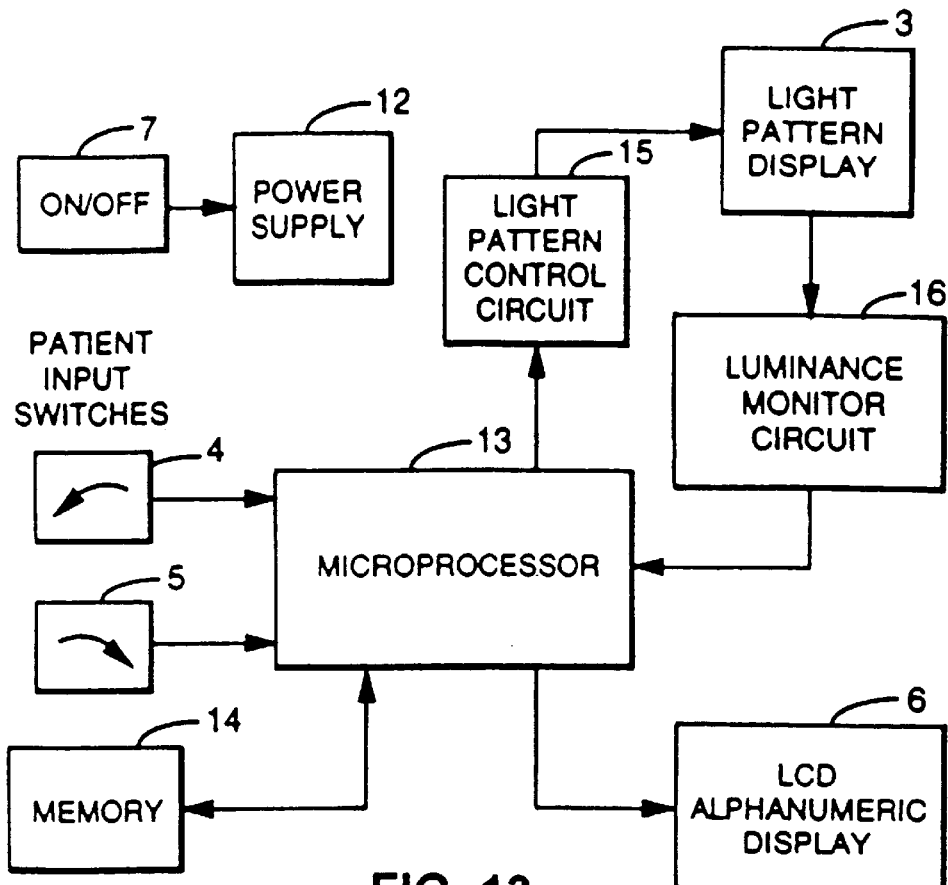
FIG. 13 is a schematic block diagram showing principal functional sections of the device of FIG. 12.

FIG. 13 is a schematic block diagram showing the principal functional sections of an embodiment including an On/Off switch 7, patient input switches 4 and 5, light pattern display 3, alphanumeric display 6, power supply 12, microprocessor 13 and associated program, memory 14, light pattern control circuit 15 and light output monitor circuit 16.

The On/Off switch 7 controls the power to the various components and starts/stops a measuring sequence. Turning on the instrument also initiates a self-diagnostic sequence that includes testing the light sources and other critical components and functions.

The light output monitor circuit 16 ensures that the light sources are functional and that their light output is within design levels. This circuit is active from the moment the instrument is turned on and throughout the measurement. The microprocessor 13 is programmed to abort the measurement and to display an informative legend in the alphanumeric display 6 if the circuit detects any fault in the light sources. This protects the user from obtaining erroneous results in the case of a failure in the operation of the light sources.

The light pattern control circuit 15 generates the sequence of the light patterns according to the specifications dictated by the microprocessor 13 and associated program.

The patient input switches 4 and 5 provide information to the microprocessor 13 as to the timing and direction of the subjective change noticed in the light pattern, e.g., the direction of apparent rotation. Each time an input switch 4 or 5 is pressed, the microprocessor 13 first checks that the correct switch has been pressed, and then reads the value of the variable light stimulus parameter existing at the moment when the switch was pressed. This parameter value information is used by the microprocessor 13 to plan the future changes in the light pattern, and to compute glucose levels, after checking for consistency of the entered data.

The microprocessor 13 executes the program, receives input from the patient input switches 4 and 5 and from the light output monitor circuit 16, reads information from, and stores information in memory 14, writes messages on the alphanumeric display 6, and provides information to the light pattern control circuit 15 about the characteristics of the light pattern to be shown on the display 3. The microprocessor can be designed and programmed in a number of different manners in accordance with programming procedures well known to those skilled in the art. The object of the microprocessor program is to efficiently utilize information provided by the user regarding the occurrence of changes in appearance of the light pattern and to coordinate all the steps, including consistency checks, repetition of stimulus presentation and calculations required to ultimately provide information to the user about the corresponding glucose level. The following section provides a specific example of a microprocessor-controlled sequence of steps that can be used to provide glucose level results, once calibration data have been entered into the memory of the device.

Measuring Sequence

Figure 14:
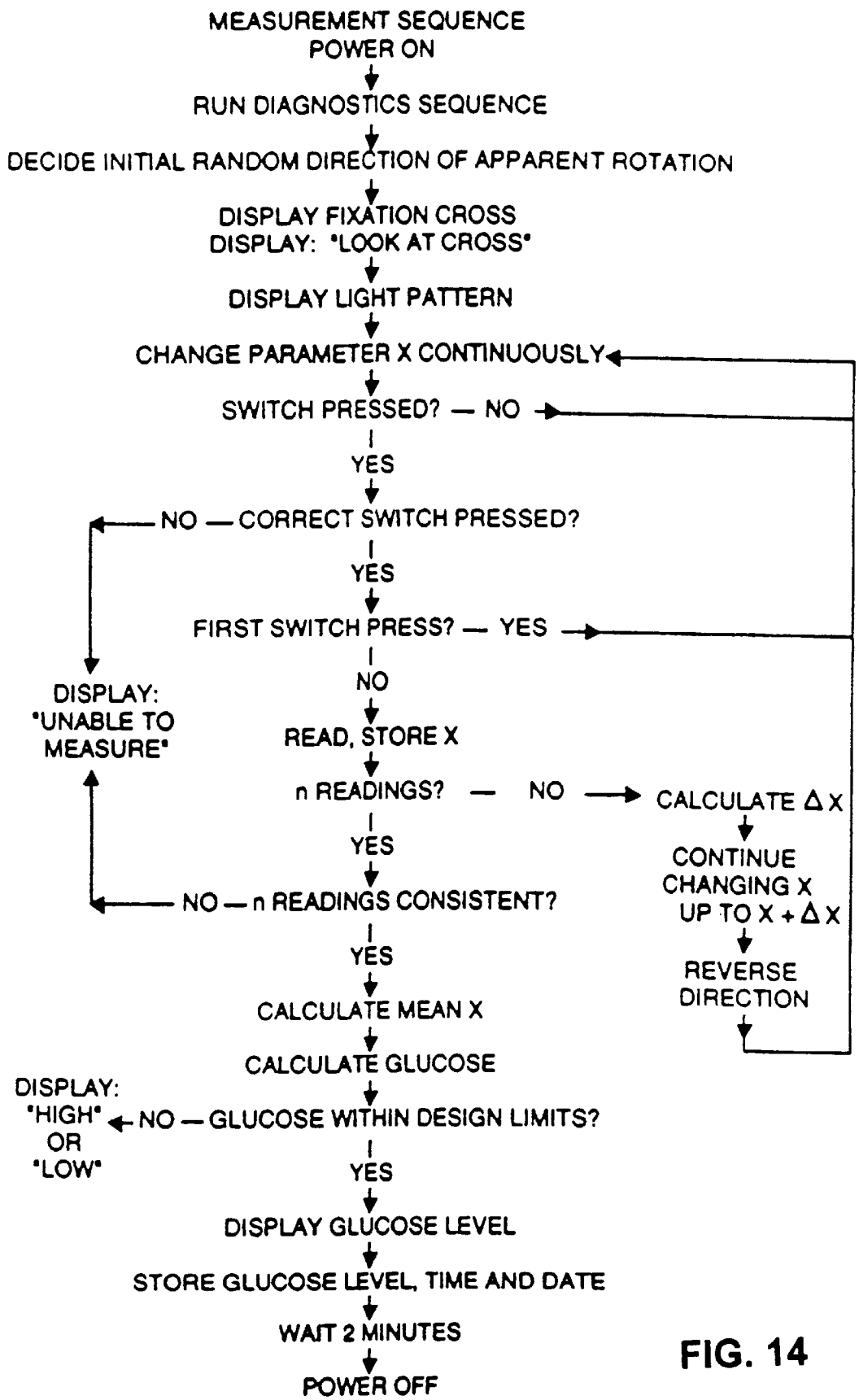
FIG. 14 is a schematic flow diagram showing steps of a diagnostic sequence.

FIG. 14 is a schematic flow diagram showing the main steps of a measuring sequence of an embodiment of the invention. This example assumes, for the sake of concreteness, that the light pattern consists of a sequence of windmill images that appear to rotate. A software program controls the execution of the sequence as is commonly done in instruments controlled by a microprocessor.

When the instrument is powered up, it first goes through a diagnostics routine which tests the integrity of its main components, including the light output of the light sources. Then the program decides randomly whether the initial direction of apparent rotation of the windmill pattern will be clockwise or counterclockwise. This direction is randomized to help avoid the possibility that the patient could influence the measurement, for example by memorizing a measurement sequence. The light pattern is then displayed and the parameter starts to change. For example, if the light pattern consists of a sequence of windmill images that appear to rotate, the parameter change could be a gradually increasing change in luminance of a set of vanes. The change continues while the program waits for a switch press actuated by the patient.

When a switch press is detected, the program analyzes whether the correct switch has been pressed. For example, the initial conditions of the light stimulus may be such that the initial expected direction of rotation is clockwise. Thus the program expects that the clockwise switch be pressed first, and that the counterclockwise and the clockwise switches be pressed in alternation afterward. If the wrong switch is pressed, which would mean either a mistake or an inconsistent response, the device is programmed to display the message "Unable to Measure". If the correct switch was pressed, the program determines if this was the first time that the switch was pressed. If this is the case, the parameter is allowed to continue changing until the patient detects a reversal. If the switch was pressed for a second time, this means that the patient has detected the first reversal, in which case the program reads and stores the value of the changing parameter at the moment of the switch press.

Figure 15:
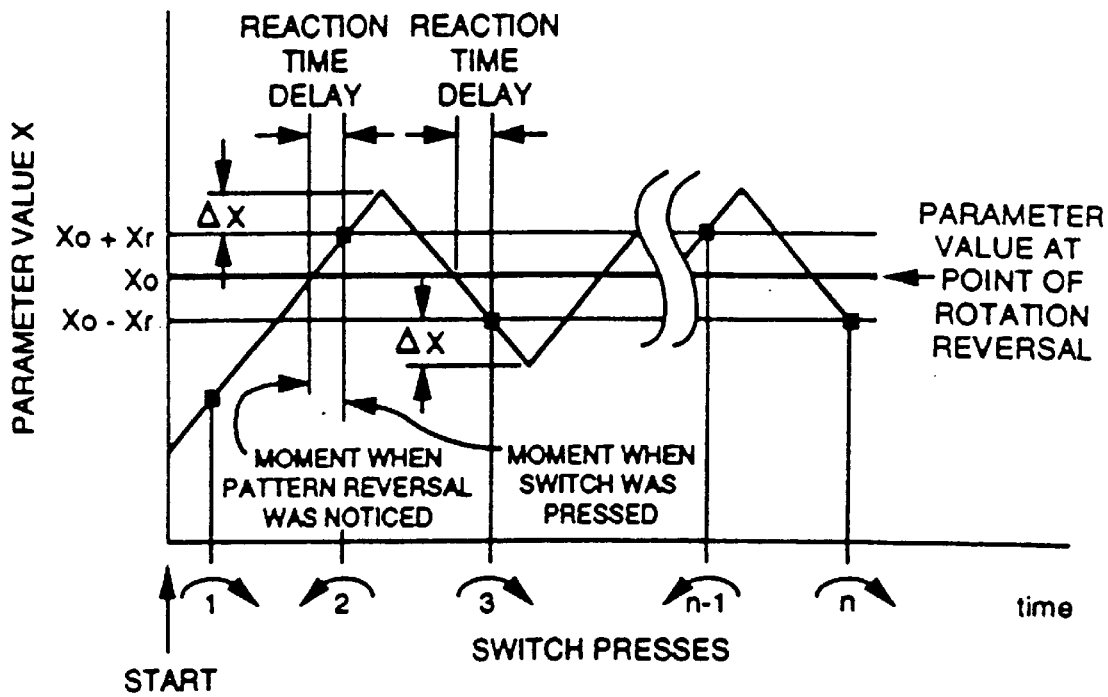
FIG. 15 is a graph demonstrating compensation for reaction time.

Compensation for the patient's reaction time is described with reference to FIG. 15. A time delay (reaction time) exists between the moment when the patient notes a reversal in the direction of rotation and the time when the patient presses the switch. Because of this delay, the parameter value read and recorded by the instrument when the switch was pressed ($X_o+X_r$) is slightly higher than the value at the point of reversal ($X_0$) (see FIG. 15). In order to remove this inaccuracy from the reading, a second point of reversal is measured, this time with the parameter changing in the opposite direction. In this example, after the patient pressed the switch to indicate the first reversal and the instrument recorded the parameter value $X_o+X_r$, the parameter is made to increase by the amount $\Delta X$ above $X_o+X_r$, and then it is made to decrease at the same rate until the patient notices a second reversal. When the patient presses the switch to indicate this second reversal, the program reads the current value of the parameter, which is now $X_o-X_r$. When the program later averages the recorded values ($X_o+X_r$) and ($X_o-X_r$), the error caused by the reaction time, $X_r$, will cancel out and the true value of the parameter at reversal, $X_o$, will be extracted. A smaller error will still remain owing to the fact that the number $X_r$ is not always the same, but has some statistical variation around a mean value. However, repeated pairs of measurements tend to cancel out this smaller error as well. Thus the feature of reversing the direction of parameter change several times during a measurement, cancels out the effect that the patient's reaction time could have on the measurements. No compensation for reaction time is necessary for a device which presents a plurality of images having different, fixed values of a parameter.

As indicated in the schematic flow diagram of FIG. 14, the program takes an even number (n) of such readings of parameter value at reversal, and then proceeds to make a consistency check of those n numbers before proceeding to calculate their average. The consistency check examines the differences between pairs of consecutive readings and determines their relative closeness. These readings should be close to each other within a factor that allows for the statistical variation of the patient's reaction time. If all the n−1 differences do not meet this criterion of closeness, the instrument cancels the reading and proceeds to display the message "Unable to Measure". This mechanism provides a safety check that prevents the possibility that either patient errors or the patient's attempts to influence the results could create erroneous readings.

Once the readings have passed the consistency check, their average is calculated. The resulting average should be close to $X_o$, the parameter value at the point of light pattern reversal, since the effect of reaction time has been removed from the measurement. This average is used to calculate corresponding glucose levels using a look up table stored in memory. The table may contain all possible pairs of appropriately rounded-off parameter values and corresponding glucose levels. Alternatively, the table may contain fewer pairs and an interpolation formula may be used to calculate intermediate values. The closest glucose level that corresponds to the averaged value of X is calculated, with an accuracy consistent with the rated accuracy of the device, for example in incremental glucose concentration units of 1 mg/dL. The pairs of parameter-glucose values will have been stored in memory at the factory, if it is determined during clinical testing that the same correspondence between parameter values and glucose levels apply to all patients. Alternatively, the numbers will be generated through a calibration procedure if it is determined that each patient requires a different correspondence between parameter values and glucose levels.

Subsequent to calculating the glucose level, the program displays the corresponding glucose value if it is within the design limits of the device; otherwise, the program displays the message "High" or "Low", depending on whether the calculated glucose value is above or below the device's design limits. The device is preferably designed to read glucose concentrations over the widest possible range, e.g., a range of 10 to 500 mg/dL with the smallest possible error, e.g., ±1%. However, a useful workable device could be designed to read over a smaller range, e.g., 40–200 mg/dL with a larger acceptable error, e.g., ±20%. Readings can be displayed in standard units used for glucose concentration, such as milligrams per deciliter(mg/dL), or millimoles per liter (mmol/L).

Lastly, the program stores the calculated glucose level in memory, along with the time and date of the measurement, for later analysis or retrieval. The program then continues to show the answer for a reasonable length of time, for example 2 minutes, and then turns itself off to preserve battery life.

This example assumed for simplicity that a single parameter in the light stimulus changed gradually. In practice, more than one parameter can change simultaneously. Multi-parameter change can provide less predictable light pattern presentations, a feature that helps avoid measurement errors caused by a patient's inconsistent responses. Multi-parameter change can also provide greater control over the range of measurement.

EXAMPLES

The following examples are put forth so as to provide those of ordinary skill in the art with a complete disclosure and description of how to carry out the methodology and make and use a device of the invention and are not intended to limit the scope of what is regarded as the invention. Efforts have been made to ensure accuracy with respect to numbers used (e.g., luminance levels, glucose concentrations, times, etc.) but some experimental errors and deviations should be expected.

Example 1

The present example illustrates one of the possible embodiments of the present invention. This example uses method a) described above for measuring the sensitivity of the visual system of a person to luminance alternations. Specifically, this example describes a light pattern whose frequency is kept constant while its luminance contrast is varied. This light pattern is used to obtain the flicker threshold of a subject, and this flicker threshold is shown to follow the subject's blood glucose levels. This example demonstrates the usefulness of this type of light pattern to determine blood glucose levels non-invasively.

A test area, which could be a screen illuminated with LED's or with other light sources, or a CRT screen, is made to change its luminance level in an alternating manner, such as shown in FIG. 1. This changing light pattern can be characterized by its mean luminance level, its contrast or modulation amplitude, the time course of the variation in luminance, the frequency of the alternations, its color, its size and its shape.

The mean luminance level is the time-averaged luminance, and can have any value within the range of luminance levels that is comfortable for viewing, for example between 1 and 100 $cd/m^2$, and in the present example should preferably be maintained substantially constant during the use of the light pattern to determine blood glucose levels. The contrast or modulation amplitude of the light pattern is the ratio of one half the peak-to-peak variation in luminance level to the mean luminance level. This contrast can have values between 0 and 1.

The time course of the variation in luminance can be a square wave with an arbitrary duty cycle, exponential, or any other shape, but should be preferably sinusoidal, and should provide an alternating, preferably regular, change in luminance. The frequency of the alternations of the luminance level can be chosen from the range of frequencies that under the right circumstances can produce the visual sensation of changes in luminance level, or approximately 0.1 to 60 Hertz. The color of the light can be any color, but is preferably red or white. The size and shape of the light pattern can be arbitrary.

The experiments reported here were conducted with a light pattern consisting of a uniformly illuminated circular field 50 mm in diameter, viewed 57 cm away, subtending 5 degrees of visual angle, red in color. The mean luminance of the field was approximately 30 $cd/m^2$. The luminance of the entire field alternated in a square-wave fashion, with 50% duty cycle, at a frequency of either 10, 20, 30 or 40 Hz.

When a person views this light pattern, the viewer may or may not see any fluctuations in brightness, depending on the contrast level of the alternations in luminance.

At zero or near zero contrast, the person sees a stable and uniform field, with no apparent alternations in brightness. At higher contrast levels, the person notices brightness alternations in the pattern, i.e. flicker. The value of the contrast at which this flicker becomes just noticeable is the threshold contrast for flicker detection, or flicker threshold for short. This flicker threshold varies with blood glucose concentration, as the following experimental data demonstrate.

FIG. 3 shows the results of 59 measurements carried out over 6 days on two subjects, one of them diabetic. In these measurements, the flicker threshold was measured by a two-alternative temporal forced choice method, while 7 different contrast values were presented to the subject in random order. The subject was required to respond, by pressing one of two buttons, whether the first or the second of two consecutive time intervals contained the light pattern with alternations in luminance. From the subject's responses, frequency-of-seeing data were obtained, showing how often the subject saw flicker at each contrast level. Typically these data go from 50% at low contrast levels, to 100% at high contrast levels. The data were fit by a Weibull function using the least squares method, and the 82% correct level of the fitted curve was taken as the flicker threshold.

Almost simultaneously with the threshold contrast measurement, blood glucose was measured with a commercial home-use blood glucose meter. The resulting data shows an approximately linear relationship between flicker threshold and blood glucose levels, over a wide range of glucose levels. Measurement errors of +/−15% are common in current blood glucose meters. FIG. 1 shows that most data points are included in the +/−15% error range. Some of the variability shown in the data of FIG. 1 is attributed to adaptation effects noticed after repeated measurements, which can be avoided by shortening the test. Some of the variability of the correlation data can also be attributed to the inherent measurement error of the blood glucose meter itself.

Figure 4:
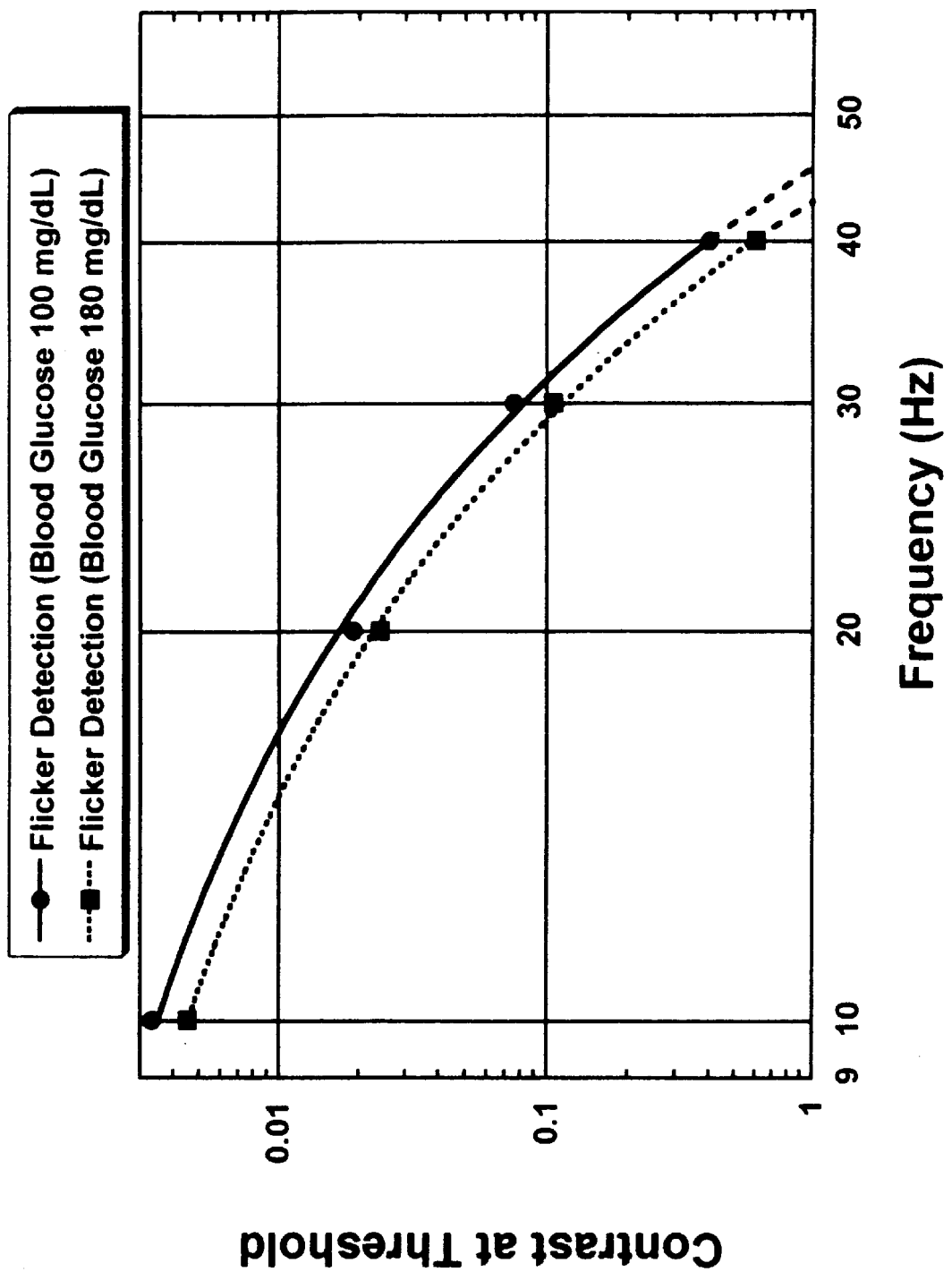
FIG. 4 is a graph illustrating the difference in crossover point at different blood glucose concentrations.
Figure 5:
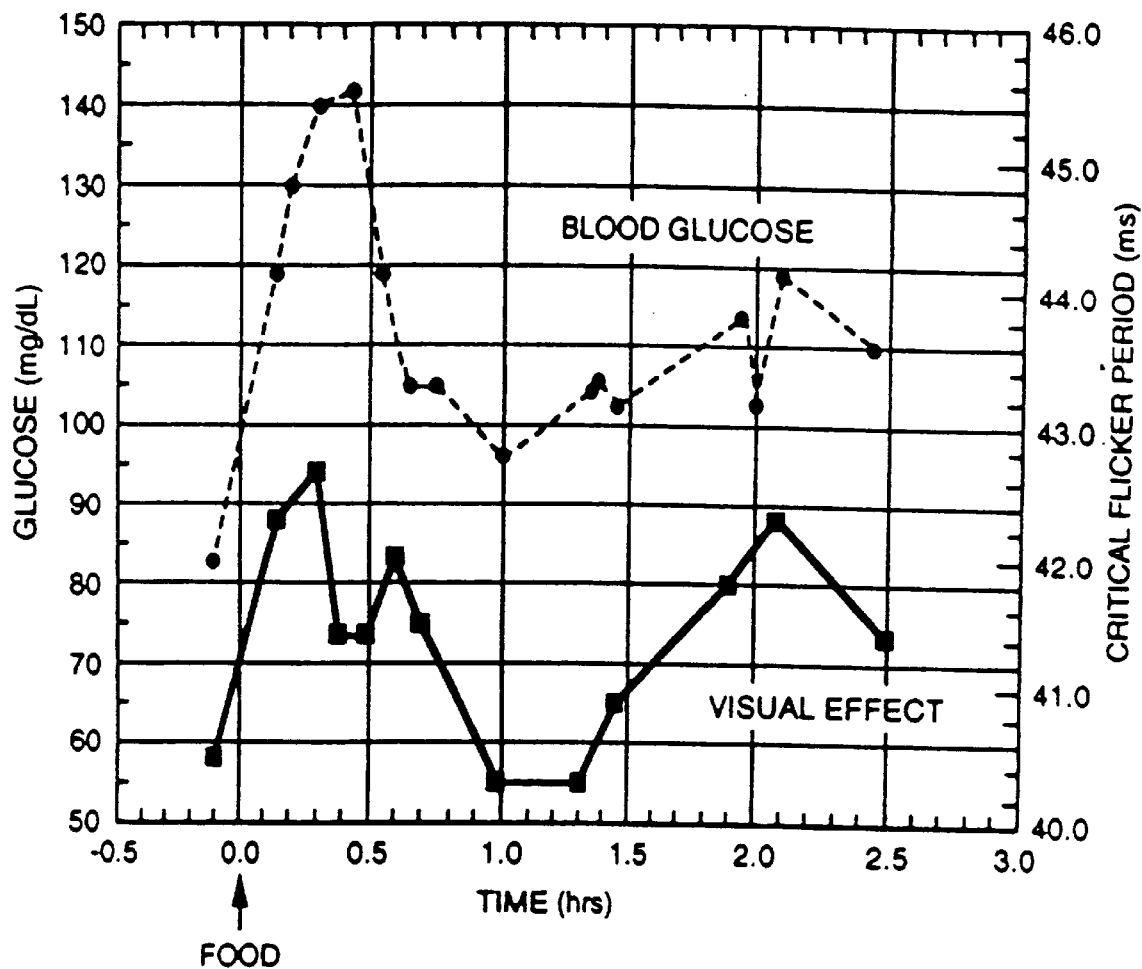
FIG. 5 is a graph showing the measured crossover point in correlation with blood glucose concentration for a first subject.
Figure 6:
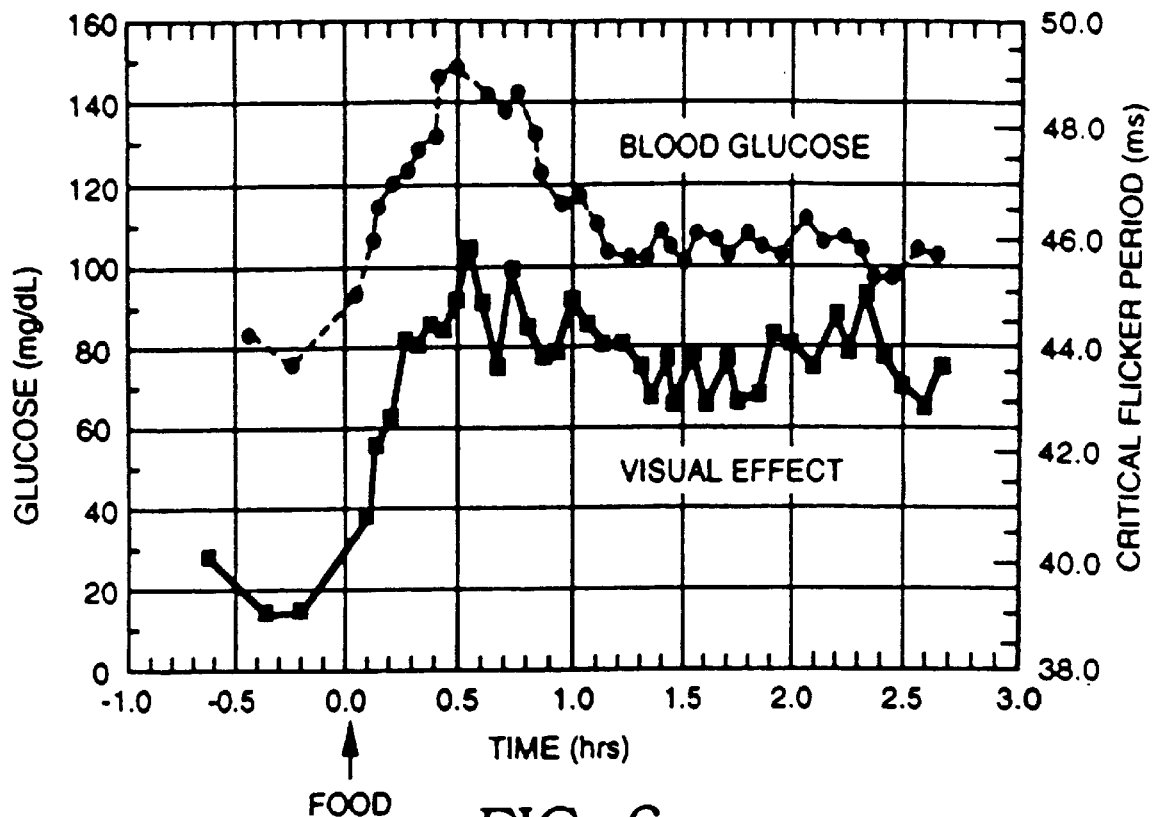
FIG. 6 is a graph showing the measured crossover point in correlation with blood glucose concentration for a second subject.
Figure 7:
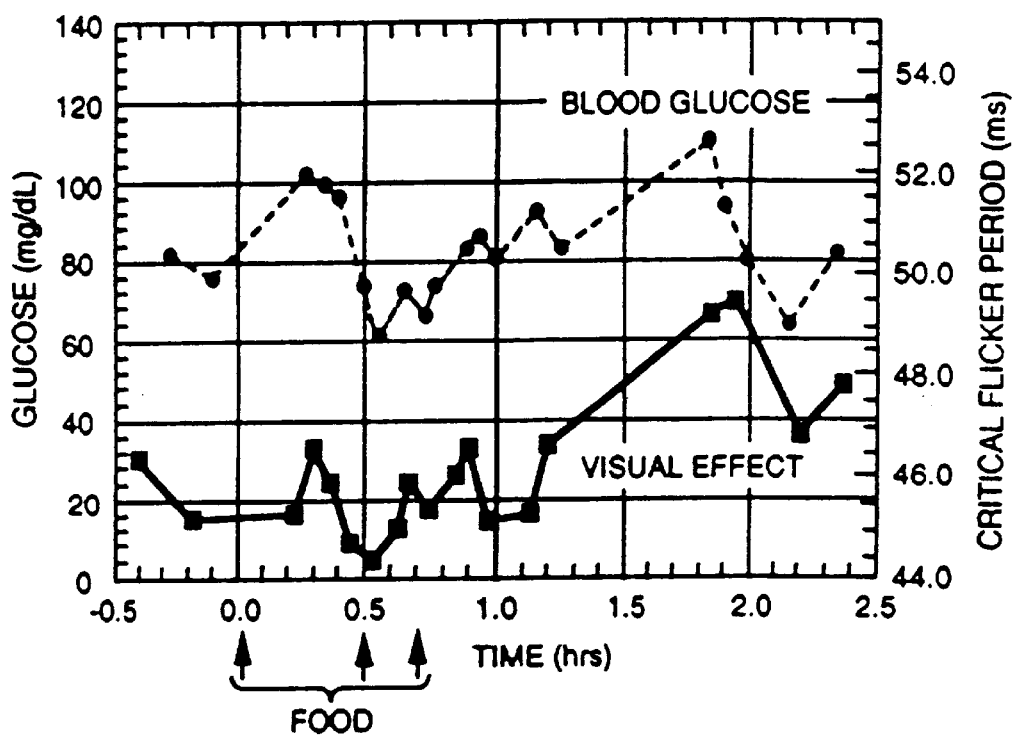
FIG. 7 is a graph showing the measured crossover point in correlation with blood glucose concentration for a third subject.
Figure 8:
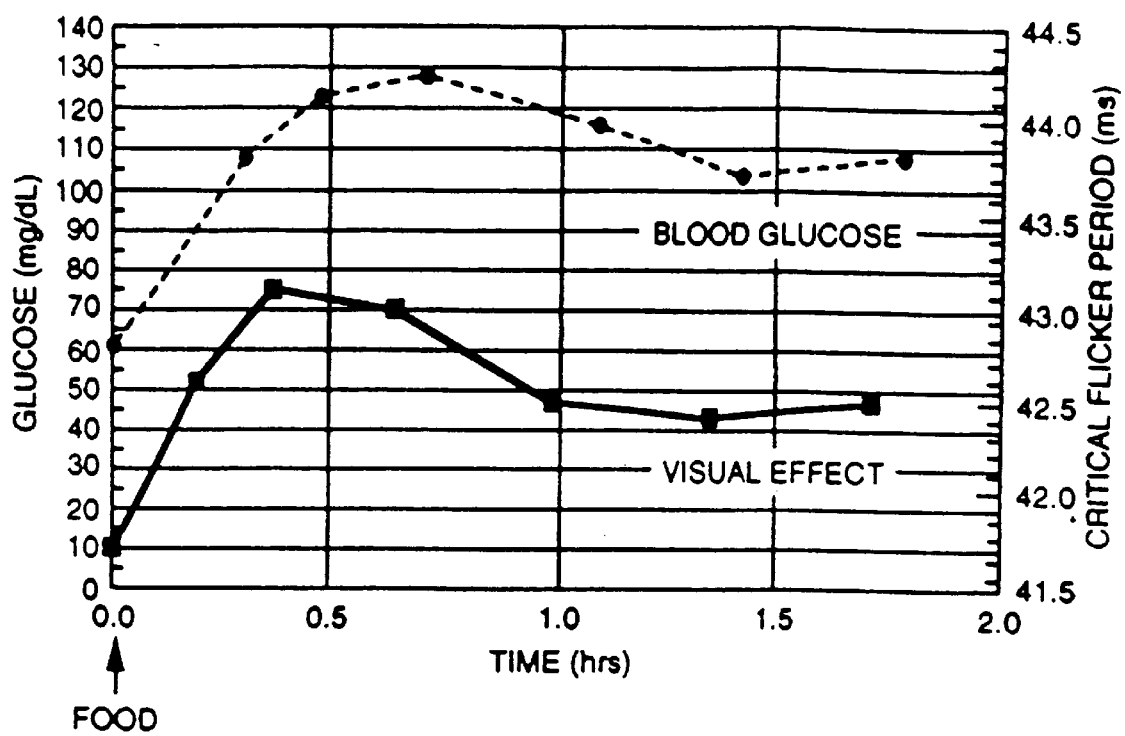
FIG. 8 is a graph showing the measured crossover point in correlation with blood glucose concentration for a fourth subject.

Other frequencies of luminance alternation in the light pattern can be used. FIG. 4 shows the results of measuring on one subject the flicker threshold at 4 different frequencies: 10, 20, 30 and 40 Hz, and at two different blood glucose levels: 100 and 180 mg/dL. The data shows an effect similar to that shown in FIG. 3: at all frequencies tested, the flicker threshold rose (moved downward in FIG. 4) when blood glucose increased.

Thus one can determine blood glucose concentration non-invasively by measuring the flicker threshold of the subject using the method explained above, or any other method known to those skilled in the art of vision testing. Then one relates the measured flicker threshold with a blood glucose value using a calibration table based on data such as that shown in FIG. 3.

Example 2

This example illustrates another possible embodiment of the present invention. This example uses method b) described above for measuring the sensitivity of the visual system of a person to luminance alternations. Specifically, this example describes a light pattern whose luminance contrast is kept constant at a level of 1, while its frequency is varied. This light pattern is used to measure the threshold frequency of a subject for the appearance of a subjective visual effect. The threshold frequency for the appearance of the subjective visual effect is shown to follow the subject's blood glucose levels. This example illustrates the usefulness of the present invention to determine blood glucose levels non-invasively.

A flash lamp controlled by a signal generator was used to create a series of light pulses with variable frequency. The frequency of the light pulses was set to change from 17 Hz to 40 Hz over 9 seconds. Thereafter, the pattern of light pulses decreased in frequency from 40 Hz to 17 Hz in 1 second. Each light pulse lasted approximately 5 milliseconds, and was effectively turned off for the remaining of the period. Thus the temporal luminance contrast of the light pattern was 1. The light pulses illuminated a white diffuser with a luminance of approximately 80 $cd/m^2$ at 40 Hz. The subject viewed the 20° illuminated field monocularly through a red filter which transmitted wavelengths above 610 nanometers.

This light pattern caused a subjective visual effect that changed with the frequency of the light pulses. Within certain range of frequencies, the subject noticed the appearance of a regular grid pattern, even though the field has no pattern but is uniformly illuminated. At another range of frequencies, the subject saw radial movement in the field, which appears to stop at a precise frequency near 25 Hz. At yet another range of frequencies, the subject experiences the presence of colors, even though the field is of a single red color. We have found that the precise frequency at which any of these subjective visual effects appears, shifts with blood glucose levels. Thus, any of these subjective effects is suitable for use in the method of the invention. The following data demonstrates this finding.

The data presented here was collected on three subjects with normal glucose metabolism and vision. The subjects pressed a switch when they noticed the desired subjective visual effect. A computer read and stored the instantaneous flicker frequency when the subject pressed the switch. Each measurement took 10 seconds to complete. The average of ten such measurement was recorded automatically as the "critical flicker period" measurement. The subjects had no knowledge of the measurement values during the experiment.

In each experiment, the subject's blood glucose level was manipulated with a normal meal following at least 6 hours of fasting. Critical flicker period measurements were made at regular intervals—every 10 to 30 minutes—starting before the meal and continuing for at least 1 hour and at most 2.5 hours after the meal. In close time proximity with these measurements, blood glucose was measured with a conventional home-use invasive blood glucose monitor.

The results obtained with different subjects are shown in FIGS. 5 through 8. Each graph shows two plots: the upper plot shows the time course of the blood glucose measurements, and the lower plot shows the time course of the critical flicker period measurements for the same subject.

The plots in FIGS. 5 to 8 show that glucose measurements and critical flicker period measurements follow a parallel time course after a glucose load. Thus the value of the flicker period when the subject noticed the desired subjective visual effect, can be used to determine blood glucose levels.

Example 3

This example illustrates another possible embodiment of the present invention, in particular an embodiment using method c) of measuring the luminance contrast sensitivity by comparing said sensitivity with the sensitivity of the visual system to another stimulus parameter.

A light pattern that contains both luminance contrast and another stimulus parameter can be designed such that the luminance contrast causes an illusion of motion in one direction, while the other stimulus parameter produces an illusion of motion in another direction. The two stimulus parameters can act as opposing "cues" for the direction of motion. The actual direction of motion of such pattern at any given time will depend on the relative strength of the two opposing cues and on the relative sensitivity of the visual system to luminance contrast and to the other parameter. The other parameter can be any other stimulus parameter, for example color contrast. The color contrast can be chosen along any direction in color space, for example in a direction that stimulates only one or more retinal cone classes.

One can use this pattern to measure the sensitivity of the visual system to luminance contrast relative to color contrast by varying the ratio of the strength of the two cues until a point of motion reversal is attained. The value of this ratio at the reversal point will shift if the sensitivity of the visual system to luminance contrast and to color contrast change relative to each other.

A pattern with circular symmetry resembling a windmill has been used successfully to implement the aforementioned method. Successive frames are presented in such a way that the luminance contrast cue (bright-dark alternations) appears to rotate in one direction while the color cue (same color vanes) appears to rotate in the opposite direction.

Figure 9:
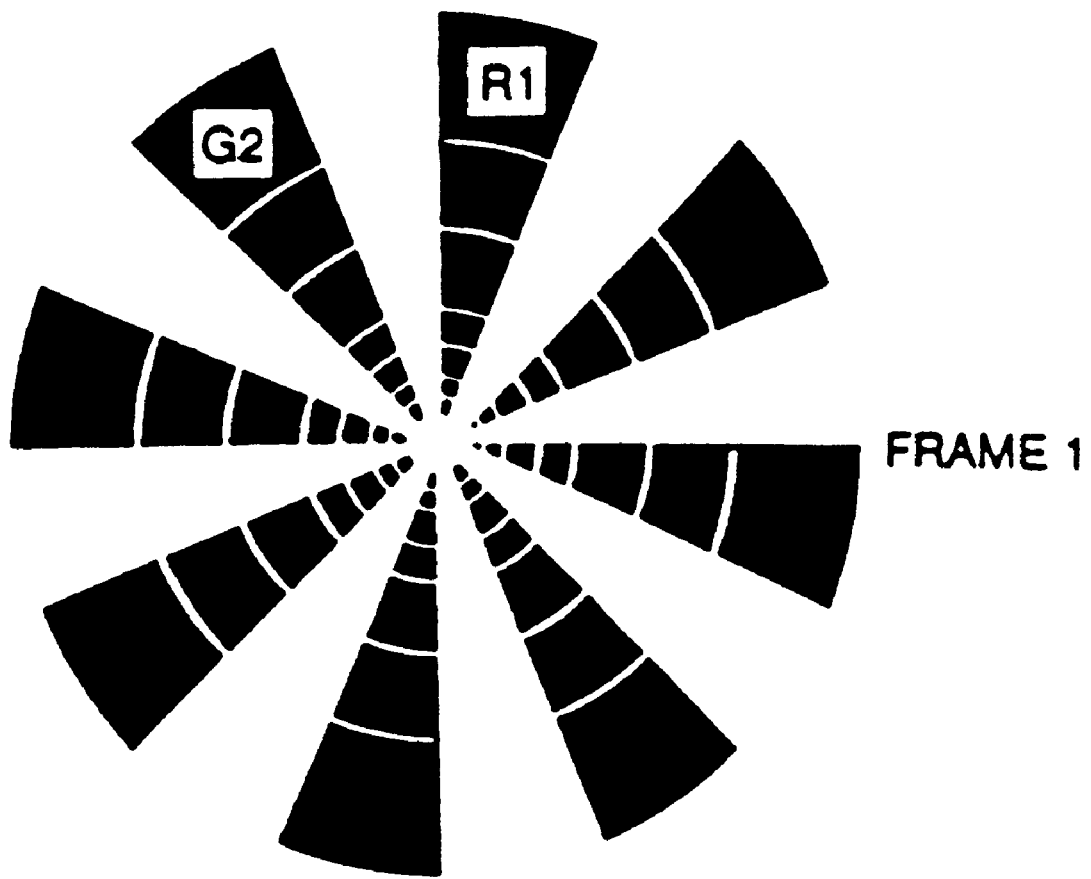
FIG. 9 is a black and white schematic view of a radial vane (windmill) light stimulus in a first position.

A specific example of a windmill pattern with 8 vanes that has been used for experimentation is depicted in FIG. 9. The vane edges can be sharp or preferably blend gradually in color and in luminance with the adjacent vane. To use this pattern, a sequence of frames each depicting the windmill pattern in a slightly different position and with slightly different colors is presented to a subject. Frame 1 has, for example, an alternation of dim red and a bright green vanes, while the next frame has an alternation of bright red and dim green vanes. The vanes in the second frame are positioned such that the vanes of the same color appear to have moved half vane in one direction, for example counter-clockwise (ccw). The third and fourth frames are identical to the first and second, except that the red and green vanes have switched positions. Sequential presentation of at least two of these frames creates the illusion of rotation. This sequence of images contains a color cue (red-ness and green-ness) that tends to produce ccw rotation, and a luminance contrast cue (the luminance difference between the dim and the bright vanes) that tend to produce clockwise (cw) rotation. The direction of apparent rotation depends on the relative strength of the two cues.

A windmill pattern similar to the one described above and shown in FIG. 9 was tested using a computer screen and projecting sequential frames or a "movie" of windmill images onto the computer monitor at a rate of 8 frames per second. The windmill outer and inner diameters were 3 and 0.25 degrees of visual angle, and was centered in a rectangular background area 8 degrees high and 10 degrees wide. The initial vane colors were red and green monitor phosphor colors, balanced to yield the same luminance for the subject. The vane colors faded gradually from red to green, passing through yellow at the border between the vanes. The mean luminance of the background and of the windmill pattern was 60 cd/m$^2$.

The luminance contrast of the vanes was set to change from 0 to 25% in 10 seconds. Thus initially, the red and green vanes had equal luminance, but as the movie progressed, one vane in each frame became brighter and the other vane dimmer than the background. The luminance difference between the dim and bright vanes rose from 0 to 25% of the mean luminance. At the start of this movie, the subject perceives with-color rotation, since the color cue is strong and the luminance contrast cue is absent. As the luminance contrast increases, a point is reached when the luminance contrast cue overcomes the color contrast cue and the apparent rotation reverses. The value of the luminance contrast at this point of reversal indicates the relative sensitivity of the visual system to luminance contrast.

A subject observed the 10-second movie and pressed a switch when the apparent rotation reversed. The value of the luminance contrast of the vanes at that moment was recorded. Blood glucose concentration was measured immediately following the visual measurement, using a commercial home blood glucose monitoring system. The procedure was repeated approximately every 15 minutes.

Figure 10:
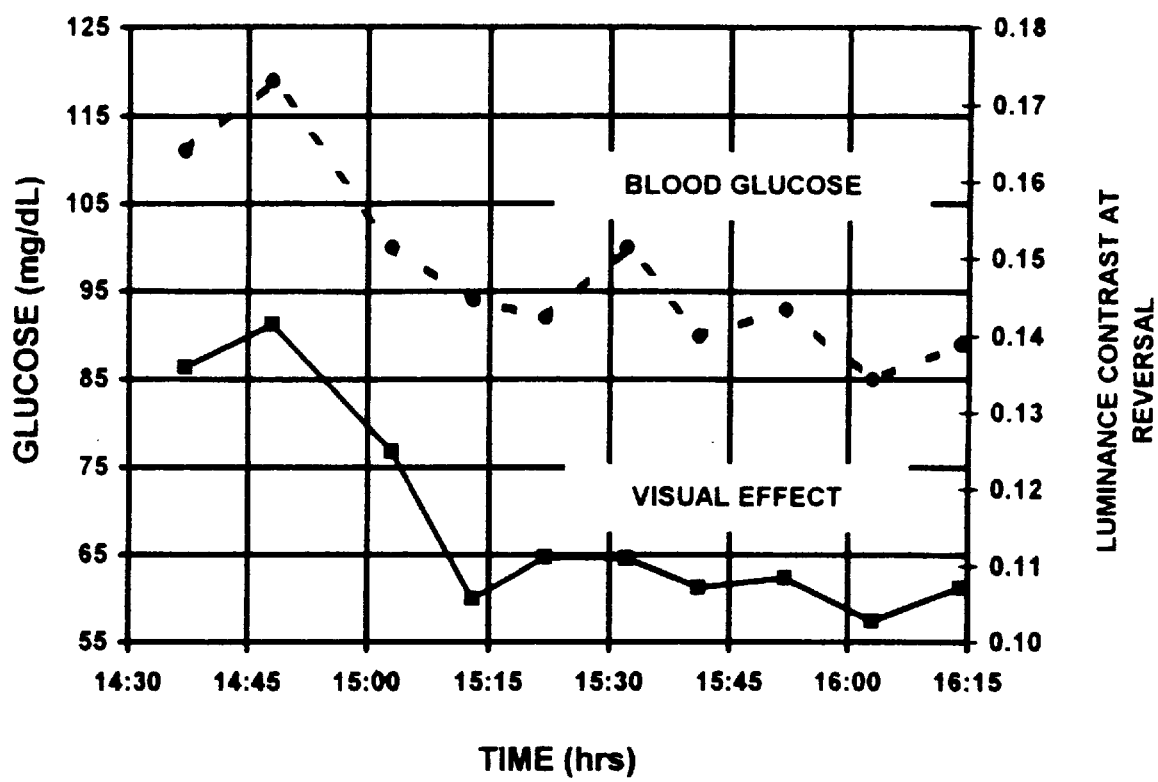
FIG. 10 is a graph showing the measured crossover point in correlation with blood glucose concentration for an observer, obtained using a windmill pattern.
Figure 11:
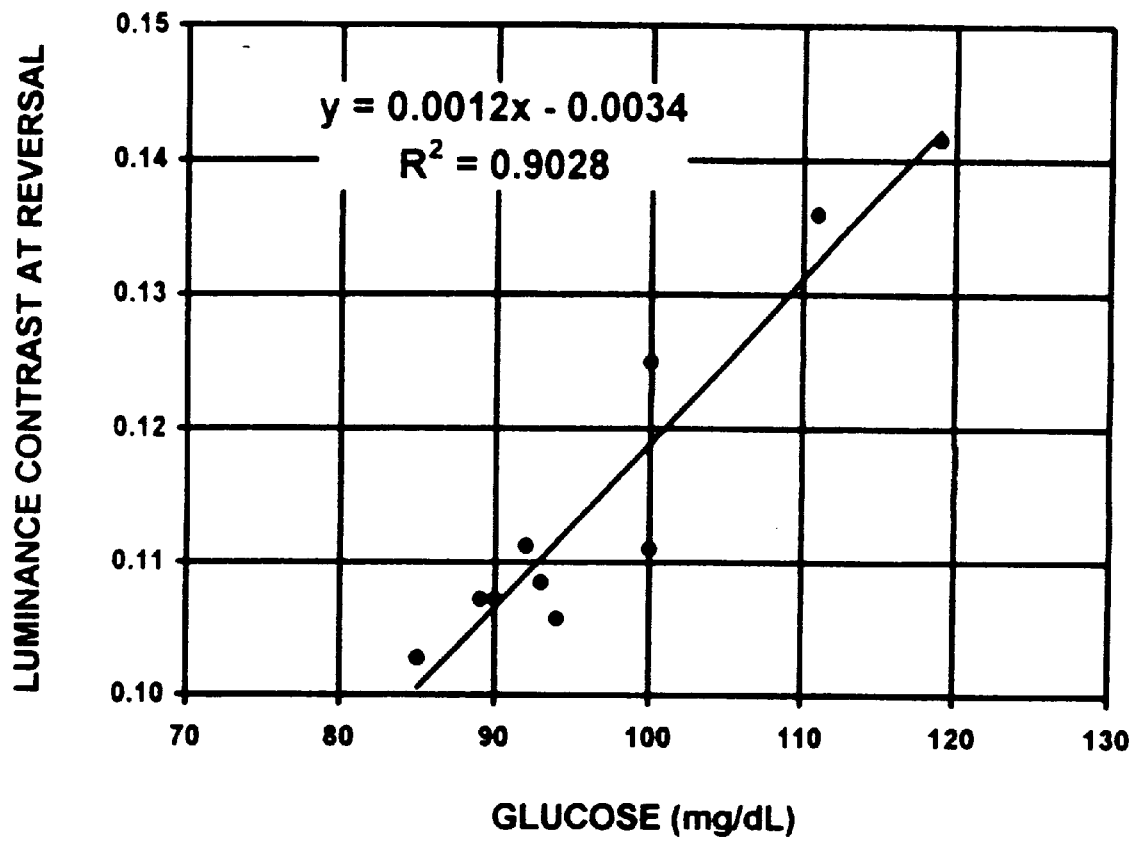
FIG. 11 is a graph showing the correlation between windmill reversal and glucose concentration.

FIG. 10 shows the results of such an experiment. The upper graph shows the time course of the blood glucose fluctuations. The lower graph shows the time course of the luminance contrast at the point of rotation reversal of the windmill. FIG. 11 shows the same data, plotted as luminance contrast vs. glucose values. This plot shows a substantially linear relationship between the two variables, indicating that in this subject, it is possible to use the contrast values at reversal to predict blood glucose values, within approximately 15% measurement error.

Variations in the windmill are possible. For example, LED's or liquid crystal displays can be used to generate the elements in the light pattern. This would allow miniaturization of the device. The background and the mean color of each frame can be a neutral white, which can give better results by avoiding color adaptation. Also, instead of the sequence of frames described earlier, in which each frame contains both the luminance contrast and the color cue, it is possible to present an alternation of two separate windmills, one that contains the luminance contrast and another that contains the color contrast. This presentation method has the advantage of producing a smoother rotation effect.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

What is claimed:

1. A method for measuring a blood glucose concentration of a subject, said method comprising:
    a) providing a light pattern which provides a first subjective characteristic and a second subjective characteristic, and can be varied from said first characteristic to said second characteristic by varying a visual parameter from a first value to a second value, said pattern having a crossover point at which said characteristic changes from said first subjective characteristic to said second subjective characteristic, where the value of said parameter at said crossover point varies with the blood glucose concentration of said subject;
    b) allowing said subject to observe said subjective visual characteristic of said light pattern; and
    c) correlating said subjective visual characteristic with said subject's blood glucose concentration.

2. The method of claim 1, wherein said pattern comprises an alternation between high luminance and low luminance, and said parameter comprises a difference between said high luminance and low luminance.

3. The method of claim 1, wherein said pattern comprises an alternation between high luminance and low luminance, and said parameter comprises a frequency of alternation.

4. The method of claim 1, wherein at least a portion of said light pattern changes over time with respect to a parameter selected from the group consisting of color, luminance level, contrast, shape, size, position, detail content, texture, speed of movement, direction of movement and rate of flicker.

5. The method of claim 1, wherein said pattern comprises a plurality of regions, each region having a different value of a parameter selected from the group consisting of color, luminance level, contrast, shape, size, position, detail content, texture, speed of movement, direction of movement and rate of flicker.

6. A device for measuring a blood glucose level of a subject, said device comprising:
    a body; and
    display means contained within said body for generating a light pattern which provides a first subjective characteristic and a second subjective characteristic, and can be varied from said first characteristic to said second characteristic by varying a visual parameter from a first value to a second value, said pattern having a crossover point at which said characteristic changes from said first subjective characteristic to said second subjective characteristic, where the value of said parameter at said crossover point varies with the blood glucose concentration of said subject;
    wherein said light pattern is selected so that it will have a first subjective visual appearance when the subject's blood glucose level is below a predetermined concentration, and will have a distinctly different appearance when the subject's blood glucose level is above said predetermined concentration.

7. The device of claim 6, wherein said display means comprises means for varying a parameter of said light pattern such that the said first subjective characteristic is changed to said second subjective characteristic.

8. The device of claim 7, further comprising:
    actuation means, which is actuated to indicate observation of a subjective visual effect;
    processor means, which is capable of measuring said parameter when actuated, and correlating said measured parameter with a corresponding blood glucose level; and
    means for displaying information about blood glucose levels.

9. The device of claim 8, wherein said light pattern is selected from the group consisting of flickering light and rotating windmill images, and said subjective visual appearance is selected from the group consisting of appearance of colors, disappearance of colors, appearance of a regular geometric pattern, disappearance of a regular geometric pattern, appearance of perceived flicker, disappearance of perceived flicker, appearance of radial movement, disappearance of radial movement, and reversal in direction of rotation.

10. The device of claim 8, wherein said processor includes information on a range of parameter values associated with the presence of a subjective visual effect, along with the corresponding blood glucose levels for said subject.

11. The device of claim 8, wherein said processor is programmed to avoid erroneous measurements by making redundant measurements, checking the consistency of the subject's responses, and canceling any effect created by the subject's reaction time.

12. The device of claim 6, wherein said display means displays said light pattern in a plurality of regions, wherein each region displays said pattern with a different value of said parameter; and further comprising:
    actuator means, enabling the subject to indicate which region corresponds to a preselected visual characteristic.

13. The device of claim 12, wherein said light pattern comprises an alternation between high luminance and low luminance, and said parameter comprises an amount of contrast between said high luminance and low luminance.

14. The device of claim 12, wherein said light pattern comprises an alternation between high luminance and low luminance, and said parameter comprises a frequency of alternation.

15. The device of claim 12, wherein said light pattern comprises a plurality of radial vane patterns, and said first and second subjective visual characteristics comprise direction of rotation.

16. A method for measuring a blood glucose concentration of a subject, said method comprising:
   a) measuring a sensitivity of a subject's visual system to alternating changes in luminance to obtain a value representing the sensitivity; and
   b) inferring from the value a blood glucose level of the subject.

17. The method of claim 16, wherein said inferring comprises comparing said value to a calibration datum.

18. The method of claim 16, wherein said measuring comprises determining the ability of the subject to detect flicker.

* * * * *